(12) United States Patent
Bjørnvad et al.

(10) Patent No.: US 6,331,426 B1
(45) Date of Patent: Dec. 18, 2001

(54) BACTERIAL GALACTANASES AND USE THEREOF

(75) Inventors: Mads Eskelund Bjørnvad, Frederiksberg; Ib Groth Clausen, Hillerød; Martin Schülein, Copenhagen; Lisbeth Bech, Hillerød; Peter Rahbek Østergaard, Virum; Carsten Sjøholm, Allerød, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/502,653

(22) Filed: Feb. 11, 2000

Related U.S. Application Data

(60) Provisional application No. 60/125,885, filed on Mar. 24, 1999, and provisional application No. 60/138,445, filed on Jun. 10, 1999.

(30) Foreign Application Priority Data

Feb. 11, 1999 (DK) .............................................. 1999 00184
Jun. 7, 1999 (DK) .............................................. 1999 00799

(51) Int. Cl.[7] .............................. C12P 21/06; C12N 9/00; C12N 9/24; C12N 9/26
(52) U.S. Cl. ......................... 435/201; 435/69.1; 435/183; 435/200; 435/252.3; 435/320.1; 536/23.2
(58) Field of Search .................................. 435/69.1, 183, 435/200, 201, 252.3, 320.1; 536/23.2

(56) References Cited

FOREIGN PATENT DOCUMENTS

| | | |
|---|---|---|
| WO 91/18521 | 12/1991 | (WO) . |
| WO 92/13945 | 8/1992 | (WO) . |
| WO 97/32013 | 9/1997 | (WO) . |
| WO 97/32014 | 9/1997 | (WO) . |

OTHER PUBLICATIONS

Henrissat, Biochem. J., vol. 280, pp. 309–316 (1991).
Emi et al., Agr. Biol. Chem., vol. 36, No. 11, pp. 1945–1954 (1972).
Braithwaite et al., Biochemistry, vol. 36, pp. 15489–15500 (1997).
Hwang et al., Food Hydrocolloids, vol. 7, No. 1, pp. 39–53 (1993).
Carpita et al., The Plant Journal, vol. 3, No. 1, pp. 1–30 (1993).
van de Vis et al., Carbohydrate Polymers, vol. 16, pp. 167–187 (1991).
Nakano et al., Agric. Biol. Chem., vol. 49, No. 12, pp. 3445–3454 (1985).
Araujo et al., Journal of Industrial Microbiology, vol. 6, pp. 171–178 (1990).
Nakano et al., Eur. J. Biochem., vol. 193, pp. 61–67 (1990).

*Primary Examiner*—Rebecca E. Prouty
*Assistant Examiner*—Manjunath N. Rao
(74) *Attorney, Agent, or Firm*—Elias J. Lambiris

(57) ABSTRACT

The invention relates to a method for modifying animal feed, in particular animal feed containing plant material such as soybean, by adding to the animal feed at least one galactanase enzyme, to a method for obtaining a DNA sequence encoding a galactanase enzyme or a portion thereof, and to isolated polynucleotide molecules encoding polypeptides having galactanase activity.

7 Claims, 4 Drawing Sheets

Multiple sequence alignment

```
Hinsolens       ------------------------------------------MRALLSTLLLGLATAVDALQYKGVDWS
Mgiganteus      ---------------------------------------------MMFVLPFLLLSFSWLASALTYKGADIS
Mthermophila    -----------------------------------------MMLTRFVAGLLGISAADAALTYRGVDWS
Aaculeatus      ----------------------------------------------MFASLLAALPLLT-HAALTYRGADIS
Bcirculans      -------------------------------------------------------LKEEAFILGMDVS
Bagaradhaerens  ----------------------------------------------------------------
Bsubtilis       MKSKVKMFFAAAIVWSACSSTGYAAAIEKEKHVSELRAEDLFVKKVEGMNKDFIKGADVS
Blicheniformis  -----------------------AHRD---SGTAKSGLYVEKVSGLRKDFIKGVDVS
Pfluorescense   ------------MKKKILAATAILLAAIANTGVADNTPFYVGADLS Hinsolens       SVMVEERAGVRYKNVNGQEKPLEYILAENGVNMVRQRVWVNPW--------DGNYNLDYN
Mgiganteus      SVPLVEQAGIKYTDG-GKVTPFENIIHNHGANTVRIRIWT---------AGDYNLQYG
Mthermophila    SVVVEERAGVSYKNTNGNAQPLENILAANGVNTVRQRVWVNPA--------DGNYNLDYN
Aaculeatus      SLLLEDEGYSYKNLNGQTQALETILADAGINSIRQRVWVNPS--------DGSYDLDYN
Bcirculans      FMDEIEQHGGSYRDENGQQEDLLTLLKMGDANAIRLRIWNDPV--------GGFCNLERT
Bagaradhaerens  ------FYD-NGVEKDALKILKDTGVNYIRLKIWEDPVNV-----GGANDLEET
Bsubtilis       SVIALENSGVTFYNTNGKRQDIFTTLKQAGVNYVRVRIWNHPYDSNGNGYGGGNNDVQKA
Blicheniformis  SIIALEESGVAFYNESGKKQDIFNTLKEAGVNYYRVRIWNDPYDANGNGYGGGNNDLEKA
Pfluorescense   YVNEMESCGATYRD-QGKKVDPFQLFADKGADLVRVRLWHNAT----WTKYSDLKDV
                      *       *            :   .   : ..   :: ::  *     :::
```

Fig. 1

```
Hinsolens        IQLARRAKAAGLGLYINFHYSDTWADPAHQTTPAGWP--SDINNLAWKLYNYTLDSMNRF
Mgiganteus       LALAKRVKAAGLTLVVDLHYSDTWADPGKQAIPSAWP--KDLDGLNTQIWQYTKDVVTSF
Mthermophila     IAIAKRAKAAGLGVYIDFHYSDTWADPAHQTMPAGWP--SDIDNLSWKLYNYTLDAANKL
Aaculeatus       LELAKRVKAAGMSLYLDLHLSDTWADPSDQTTPSGWST-TDLGTLKWQLYNYTLEVCNTF
Bcirculans       VAVAKRVKEHGLHFLLDFHYSDRWADPANQWKPKAWEK-LSYEELQRAVCNYTADVLRTL
Bagaradhaerens   VTMAQRVKEHDMGFLLNFHYSNFWADPERQNKPTAWED-LTFDELVDVYDHTAETLQVL
Bsubtilis        IEIGKRATANGMKVLADFHYSDFWADPAKQKVPKAWAN-LSFEAKKAKLYEYTKQSLQKM
Blicheniformis   IQIGKRANANGMKLLADFHYSDFWADPAKQKAPKAWAN-LNFEDKKTALYQYTKQSLKAM
Pfluorescense    SKTLKRAKNAGMKTLLDFHYSDTWTDPEKQFIPKAWAHITDTKELAKALYDYTTDTLASL
                    *  .    .    :*: :*   *      *    *    . .       :  . ..

Hinsolens        ADAGIQVDIVSIGNEITQGLLWPLGKTNN-------WYNIARLLHSAAWGVKDSRLNP
Mgiganteus       ANQGTPIDILQVGNEINNGLLWPVGEISSNG-----INPVSQLLHSAINGAKAAGN--
Mthermophila     QNAGIQPTIVSIGNEIRAGLLWPTGRTEN-------WANIARLLHSAAWGIKDSSLSP
Aaculeatus       AENDIDIEIISIGNEIRAGLLWPLGETSS-------YSNIGALLHSGAWGVKDSNLAT
Bcirculans       KEHDALPDMVQVGNEITPGMLWDEGRVSGEEHDTDEQ-WERFAGLVKYGIAAVKSVDSE-
Bagaradhaerens   EEVDGLPDMIQIGNEIQSGMLWPDGKTWGEEQGVDYGGFENLLQLVNAGIDAVHDTLPEN
Bsubtilis        IKEGVDIGMVQVGNETT------GGFAGETD-----WTKMCQLFNEGSRAVRETNSN-
Blicheniformis   KAAGIDIGMVQVGNETN------GGLAGETD-----WAKMSQLFNAGSQAVRETDSN-
Pfluorescense    DQQQLLPNLVQVGNETNIEILQAEDTLVHGIPN----WQRNATLLNSGVNAVRDYSKKT
                 :  :   :    *.:**      GGXAGETD          .       .

Fig. 1
```

```
Hinsolens       -K-PKIMVHLDNGWNWDTQNWWYTNVLSQGPFEMSDFDMMGVSFYPFYSASATLDSLRRS
Mgiganteus      ---PKILIHLANGWDWSGLNSFFGKVFIPGALSADEVDIIGVSFYPFYDAGATLSALKSS
Mthermophila    -K-PKIMIHLDNGWDWGTQNWWYTNVLKQGTLELSDCDMGVSFYPFYSSSATLSALKSS
Aaculeatus      -T-PKIMIHLDDGWSWDQQNYFYETVLATGELLSTDFDYFGVSYYPFYSASATLASLKTS
Bcirculans      ---IKIMIHIDRGGDNAESRKFYDRFEALG----V-EFDIIGLSYYPWWHG--TLDALRDN
Bagaradhaerens  HS-VEIMLHLADGGDNDLYRWWFDEMLAHG----VHDFDVIGLSYYPYWHG--SLNDLQAN
Bsubtilis       ---ILVALHFTNPETAGRYSFIAETLSKNK----V-DYDVFASSYYPFWHG--TLQNLTSV
Blicheniformis  ---ILVALHFTNPETSGRYAWIAETLHRHH----V-DYDVFASSYYPFWHG--TLKNLTSV
Pfluorescense   GKPIQVVLHIAQPEN---ALWWFKQAKENG---VIDYDVIGLSYYPQWSEY-SLPQLPDA
                     : :*              .    *        :  * ::* ::   . :*
                                                          SYYPXWHG Hinsolens       LNNMVSRWGKEVAVVETNWPTSCP---YPRYQFPAD--VRN-VPFSAAGQTQYIQSVANV
Mgiganteus      LANLANTFKKPIVVAETDWPVACS---GVKLTEPS------VPVSTSGQQTWIGDIKNV
Mthermophila    LDNMAKTWNKEIAVVETNWPISCP---NPRYSFPSD--VKN-IPFSPEGQTTFITNVANI
Aaculeatus      LANLQSTYDKPVVVVETNWPVSCP---NPAYAFPSD--LSS-IPFSVAGQQEFLEKLAAV
Bcirculans      LHDLAERYGKPINVVETAYPWTLEQPDGHEWILNQEELLPGYPASVEGQTRYLKDLLQI
Bagaradhaerens  LNDISERYNKDVIVVETSYAHTLEEGDGFPNIFGTEEEVEGGYPATVEGQTAFLEDVMSV
Bsubtilis       LKAVANTYGKKVMVAETSYTYTAEDGDGHGNTAPKSGQTLP-YPISVQGQATAVRDVMEA
Blicheniformis  LTSVADTYGKKVMVAETSYTYTAEDGDGHGNTAPKNGQTLN-NPVTVQGQANAVRDVIQA
Pfluorescense   IAELQNTYHKPVMIVETAYPWTLHNFDQAGNVLGEK-AVQPEFPASPRGQLTYLLTLTQL
                 .   .   *     **: * :           .           .  ** *
                                    YxxTxExxDG
```

Fig. 1

```
Hinsolens       VSSVSKGVG--LFYWEPAWIHN-------------------------------------ANLGSS------
Mgiganteus      LQSLPNGLGQGIFYWEPGWIGN-------------------------------------ANLGSG------
Mthermophila    VSSVSRGVG--LFYWEPAWIHN-------------------------------------ANLGSS------
Aaculeatus      VEATTDGLG--VYYWEPAWIGN-------------------------------------AGLGSS------
Bcirculans      VREVPGGLGAGFYYWEPAWIPS-------KE----------------------------E-WSVG-----
Bagaradhaerens  IHGVPNDHGRGFFYWEPTWIPA-------EN----------------------------AGWKDG-----
Bsubtilis       VANT-GKAGLGVFYWEPAWIPVGPKTQIEKNKVLWETYGSGWASSYAAEYDPEDAGKWYG
Blicheniformis  VSDV-GEAGIGVFYWEPAWIPVGPAHRLEKNKALWETYGSGWATSYAAEYDPEDAGKWFG
Pfluorescense   VKSA-GGMG--VIYWEPAWVSTR-------CR---------------------------TLWGKG-----
                 :   .       . **** *                                         .

Hinsolens       --CADNTMFT---PSGQALSSLSVFHRI-------------------------
Mgiganteus      --CSDNLLVS---SNGATRDSINIFNQM-------------------------
Mthermophila    --CADNTMFS---QSGQALSSLSVFQRI-------------------------
Aaculeatus      --CADNLMVDY--TTDEVYESIETLGEL-------------------------
Bcirculans      ----GNLTMFD--FKGQKLQSFSALKAGLENETEWDEQPNAALIK
Bagaradhaerens  ------DNQTLFD--FDGNALPSLKIFN-------------------------
Bsubtilis       GSAVDNQALFD--FNGHPLPSLQVFQYAESGHIPKKR----------------
Blicheniformis  GSAVDNQALFD--FKGRPLPSLHVFQYVDTGTPFKN-----------------
Pfluorescense   ----ENASFFDATRKNNALPAFLFFKADYQASAQAE-----------------
                      *         .                ::
                              NxxLFD--FxGxxLxS
```

Fig. 1

BACTERIAL GALACTANASES AND USE THEREOF

CROSS-REFERENCE TO RELATED APPLICATIONS

This application claims priority under 35 USC 119 of U.S. provisional application numbers 60/125,885 filed Mar. 24, 1999 and 60/138,445 filed Jun. 10, 1999 and of Danish application nos. PA 1999 00184 filed Feb. 11, 1999 and PA 1999 00799 filed Jun. 7, 1999, the contents of which are fully incorporated herein by reference.

BACKGROUND OF THE INVENTION

1. Field of the Invention

The present invention relates to bacterial galactanase enzymes for use in different industrial applications, such as in the textile, detergent and cellulose fiber processing industries, and in particular to methods for modifying animal feed using such enzymes.

2. Description of the Related Art

Galactans and arabinogalactans are present in most plants as components of pectic hairy regions and can be found in high quantities e.g. in soy plant seed and in potatoes. Another good source for highly purified galactans and arabinogalactans is the water-soluble polysaccharide extracted with alkali from lupin fibre. This substrate can be treated with arabinofuranosidase (EC 3.2.1.55) resulting in a galactan with a very high content of galactose (more than 91%); such a substrate can be obtained from Megazyme, Australia.

Galactans and arabinogalactans are usually attached to O-4 of rhamnose residues in the rhamnogalacturonan backbone of the hairy region. The distribution and composition of the side chains vary considerably between different cell types and physiological states, but in general about half of the rhamnosyl units in the rhamnogalacturonan regions have side chains attached. The galactan side chains are in most plants type 1 galactans, which are composed of β-1,4 linked galactopyranose with some branching points and a length of up to 60 saccharide units (DP60). Arabinofuranose residues or short arabinan oligomers can be attached to the galactan chain at the O -3 of the galactosyl unit, thus the name arabinogalactan. Galactans (or arabinogalactans) have an important function in the primary cell wall, where they interact with other structural components of the cell wall such as xyloglucans or arabinoxylans. Thus, they possibly serve to anchor the pectic matrix in the cell wall. Furthermore, they increase the hydration and water-binding capacity and decrease inter-chain association between pectin polymers, which is thought to be of importance for modulation of porosity and passive diffusion. (Carpita & Gibeaut, 1993, Plant J.,3, 1–30; O'Neill et al., 1990, Methods in Plant Biochemistry, 415–441; Selvendran, 1983, The Chemistry of Plant Cell Walls. Dietary Fibers; Hwang et al., Food Hydrocolloids, 7, 39–53; Fry, 1988, The Growing Plant Cell Wall: Chemical and Metabolic Analysis).

Beta-1,4-galactanases (EC 3.2.1.89) degrade galactans (and arabinogalactans) and have been purified from a variety of microbial sources (Nakano et al., 1985, Agric. Biol. Chem.,49, 3445–3454; Emi & Yamamoto, 1972, Agric. Biol. Chem., 36, 1945–1954; Araujo & Ward, 1990, J. Ind. Microbiol., 6, 171–178; Van De Vis et al., 1991, Carbohydr. Polym., 16, 167–187).

WO 92/13945 describes cloning and DNA sequencing of a fungal beta-1,4-galactanase from *Aspergillus aculeatus*.

WO 97/32014 describes cloning and DNA sequencing of fungal beta-1,4-galactanase from Humicola insolens and *Myceliophthora thermophilum*.

WO 97/32013 describes cloning and DNA sequencing of fungal beta-1,4-galactanase from *Meripilus giganteus*.

Braithwaite et al., BIOCHEMISTRY Vol. 36 , No. 49 pp. 15489–15500 (1997) disclose a galactanase from Pseudomonas fluorescens ssp. cellulose which is a retaining family 53 glycosyl hydrolase in which e161 and e270 are the catalytic residues.

WO 91/18521 describes a feed composition comprising, as a source of carbohydrates, a mannan-containing hemicellulose selected from soybeans, corn and alfalfa, as well as a mannanase that catalyzes the degradation of the mannan-containing hemicellulose.

Nakano et al., Eur. J. Biochem. 193(1): 61–67 (1990) describes the purification and characterization of an exo-1, 4-β-galactanase from a strain of *Bacillus subtilis*.

The database entries from the publicly available databases EMBL and Swissprot listed below refer to sequences with homology to the galactanases described herein:

| Species | Description | wissprot/TREMBL | EMBL Entry |
|---|---|---|---|
| Bacillus subtilis | Hypothetical protein | 007013, 032260 | Z94043, Z99121 |
| Bacillus circulans | Hypothetical protein | P48843 | L03425 |

The galactanases in the list above and the galactanases of the invention belong to family 53 of glycosyl hydrolases (Henrissat B., A classification of glycosyl hydrolases based on amino-acid sequence similarities. Biochem. J. 280: 309–316 (1991)).

In spite of the state of the art e.g. as disclosed above, there remains a need for galactanase enzymes with improved activity for a number of different purposes. The object of the present invention is to provide galactanase enzymes with a high galactanase activity for use in industrial applications, such as the textile, detergent and cellulose fiber processing industries, and in particular for the modification of animal feed.

SUMMARY OF THE INVENTION

The inventors have now found that certain bacterial galactanases, in particular derived from a number of Bacillus species, have advantageous properties that make them suitable for use in the modification of animal feed and in other industrial applications.

In one aspect, the present invention relates to a method for modifying animal feed, the method comprising adding to the animal feed at least one galactanase enzyme comprising at least one consensus amino acid sequence selected from the group consisting of amino acid sequences SEQ ID NO 1–6:

```
                                            (SEQ ID NO.1)
    Y-x-x-T-x-E-x-x-D-G (SEQ ID NO.2)
    N-x-x-(M/L)-F-D-F-x-G-x-x-L-x-S (SEQ ID NO.3)
    S-Y-Y-P-x-W-H-G
```

-continued

```
                                         (SEQ ID NO.4)
YD(S/A)NGNGYGG (SEQ ID NO.5)
VGP(K/A) (T/H) (Q/R) (I/L)EKNK(V/A)LWETYGS-
GWA(S/T) SYAAEYDPEDAGKW(Y/F)GGSAV (SEQ ID NO.6)
GG(F/L)AGETD
``` where x represents any amino acid.

Further aspects of the invention relate to methods for modifying animal feed using other galactanase enzymes as defined below, as well as a method for obtaining a DNA sequence s encoding a galactanase enzyme or a portion thereof, and isolated polynucleotide molecules encoding polypeptides having galactanase activity.

The inventors found novel enzymes having substantial galactanase activity, i.e. an enzyme exhibiting galactanase activity which may be obtained from a bacterial strain of the genus Bacillus, more specifically of the strain *Bacillus licheniformis* ATCC 14580 or *Bacillus agaradhaerens* AC13 (DSM 8721), and have succeeded in identifying DNA sequences encoding such enzymes. The DNA sequences and the deduced amino acid is sequences are listed in the sequence listing as SEQ ID NO. 7 and 8, as well as SEQ ID NO. 11 and 12, respectively.

In a further aspect of the invention there is provided an expression vector comprising a polynucleotide sequence as defined in the previous aspects.

Within yet another aspect of the present invention there is provided a cultured cell into which has been introduced an expression vector as disclosed above, wherein said cell expresses the polypeptide encoded by the DNA segment.

A further aspect of the present invention provides an isolated polypeptide having galactanase activity selected from the group consisting of (a) polypeptide molecules comprising an amino acid sequence as shown in SEQ ID NO.8 from residue 1 to residue 399; and (b) polypeptide molecules that are ar least 80% identical to the amino acids of SEQ ID NO.8 from amino acid residue 1 to amino acid residue 399.

One other aspect of the present invention provides an isolated polypeptide having galactanase activity selected from the group consisting of (a) polypeptide molecules comprising an amino acid sequence as shown in SEQ ID NO.12 from residue 1 to residue 245; and (b) polypeptide molecules that are ar least 80% identical to the amino acids of SEQ ID NO.12 from amino acid residue 1 to amino acid residue 245.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

Within another aspect of the present invention there is provided an enzyme preparation comprising a purified polypeptide according to the invention; and also such a preparation which further comprises one or more enzymes selected from the group consisting of proteases, cellulases (endoglucanases), β-glucanases, hemicellulases, lipases, peroxidases, laccases, α-amylases, glucoamylases, cutinases, pectinases, reductases, oxidases, phenoloxidases, ligninases, pullulanases, arabinosidases, mannanases, xyloglucanases, xylanases, pectin acetyl esterases, polygalacturonases, rhamnogalacturonases, pectin lyases, pectate lyases, pectin methylesterases, cellobiohydrolases, transglutaminases; or mixtures thereof.

The novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme preparation or an enzyme of the invention having substantial galactanase activity; to use of an enzyme of the invention for the treatment of cellulose-containing fibers, yarn, woven or non-woven fabric, for the degradation or modification of plant material; to use of an enzyme of the invention in wine or juice processing.

The enzyme of the invention is very effective for use in an enzymatic scouring process in the preparation of cellulosic material e.g. for proper response in subsequent dyeing operations. Further, it is contemplated that detergent compositions comprising the novel enzyme are capable of removing or bleaching certain soils or stains present on laundry, especially soils and spots resulting from galactan or arabinogalactan containing food, plants, and the like. It is also contemplated that treatment with detergent compositions comprising the novel enzyme can prevent binding of certain soils to the cellulosic material.

Definitions

The term "ortholog" (or "species homologue") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and/or terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expression" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic environment and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example Dynan and Tijan, Nature 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form. Even more preferably, the protein is provided in a highly purified form, i.e. greater than 80% pure, more preferably greater than 95% pure, and even more preferably greater than 99% pure, as determined by SDS-PAGE.

The term "isolated protein/polypeptide may alternatively be termed purified protein/polypeptide".

The term "homologous impurities" means any impurity (e.g. a polypeptide other than the polypeptide of the invention) which originates from the homologous cell where the polypeptide of the invention is originally obtained from.

The term "obtained from" as used herein in connection with a specific microbial source means that the polynucleotide and/or polypeptide is produced by the specific source, or by a cell in which a gene from the source has been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that is encodes a polypeptide). Degenerate codons contain different triplets of nucleotides, but encode the same amino acid residue (for example, GAU and GAC triplets both encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

In the present context, the term "galactanase" is defined according to the Enzyme Classification (EC) as having the EC-number 3.2.1.89, the official name arabinogalactan endo-1,4 -beta-galactosidase, the alternative names endo-1, 4-beta-galactosidase, galactanase and arabinogalactanase, and catalyzing the reaction: endohydrolysis of 1,4-beta-D-galactosidic linkages in arabinogalactans.

DETAILED DESCRIPTION OF THE INVENTION

Comparison of different galactanase amino acid and DNA sequences was done with the program "align" was used to calculate individual amino acid and DNA homologies for a number of different galactanase enzymes of both bacterial and fungal origin. The enzymes were isolated from the following microorganisms: Aspergillus aculeatus, Bacillus agaradhaerens, Bacillus circulans, Bacillus licheniformis, Bacillus subtilis, Humicola insolens, Meripilus giganteus, Myceliophthora thermophila and Pseudomonas fluorescens.

"align" is a full Smith-Waterman alignment, useful for both protein and DNA alignments. The default scoring matrices BLOSUM50 and the identity matrix are used for protein and DNA alignments, respectively. The penalty for the first residue in a gap is –12 for proteins and –16 for DNA. While the penalty for additional residues in a gap is –2 for proteins and –4 for DNA. Align is from the fasta package version v20u6 (William R. Pearson, Department of Biochemistry, Box 440, Jordan Hall University of Virginia, Charlottesville, Va., USA).

Multiple alignments of protein sequences were done using "clustalw" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680).

Multiple alignment of DNA sequences were done using the protein alignment as a template, replacing the amino acids with the corresponding codon from the DNA sequence.

The homologies obtained were as follows (where DNA homologies are read from the top and amino acid homologies are read from the left):

| Protein\DNA | B. agaradhaerens | B. circulans | B. licheniformis | B. subtilis |
|---|---|---|---|---|
| B. agaradhaerens | 100.0 | 51.5 | 47.8 | 45.0 |
| B. circulans | 43.6 | 100.0 | 49.9 | 47.5 |
| B. licheniformis | 31.3 | 31.5 | 100.0 | 69.4 |
| B. subtilis | 29.0 | 29.9 | 72.5 | 100.0 |

DEFINITION OF UNIQUE REGIONS

The table above suggests that the Bacillus galactanases, which are of particular interest according to the present invention, fall into two basic structural classes as follows:
a) The homologies show that the B. subtilis amino acid sequence has a higher overall homology to B. licheniformis than to the B. circulans/B. agaradhaerens sequences.

b) Similarly, the homologies show that the *B. agaradhaerens* amino acid sequence has a higher overall homology to *B. circulans* than to the *B. subtilis/B. licheniformis* sequences.

BRIEF DESCRIPTION OF FIGURE

The attached FIG. 1 shows a multiple sequence alignment of the amino acid sequences from the four Bacillus species mentioned above as well as certain fungal galactanases. The full-length DNA sequences from *B. circulans, B. agaradhaerens, B. subtilis* and *B. licheniformis*, are shown in SEQ ID NO.9, SEQ ID NO.11, SEQ ID NO.13 and SEQ ID NO.7, respectively. In addition to illustrating the differences between the *Bacillus galactanases* on the one hand and the fungal galactanases on the other hand, it is evident from the amino acid sequence alignment of FIG. 1 that the respective pairs of Bacillus enzymes share certain structural elements pairwise.

In the following, protein motifs characterizing one or more Bacillus galactanases identified by the inventors are listed. Residues in brackets denote more than one possibility in a given position. An "N" in a given position denotes any nucleotide in that position.

1) Motif characterizing all *Bacillus galactanases*:

Y-x-x-T-x-E-x-x-D-G (SEQ ID NO.1)

with the following DNA sequences (SEQ ID NO's. 15–18, respectively):

B. subtilis 5'-TACACCTATACCGCTGAGGATGGCGATGGG-3'

B. licheniformis 5'-TATACGTATACGGCTGAAGACGGAGACGGA-3'

B. agaradhaerens 5'-TATGCTCACACATTGGAAGAGGGGATGGT-3'

B. circulans 5'-TATCCTTGGACACTGGAGCAACCTGATGGC-3' and the following consensus primer (SEQ ID NO.19):

5'-TA(C/T)NCN(T/C) (A/G)NACNN(C/T) (T/G)GA(G/A) (G/C)AN(G/C) (G/C)NGA(T/C)GGN-3'

2) Motif characterizing all *Bacillus galactanases*:

N-x-x-(M/L)-F-D-F-x-G-x-x-L-x-S (SEQ ID NO.2)

or, more specifically:

N(Q/L)(T/A)(M/L)FDFXGXXL(P/Q)S (SEQ ID NO.20)

with the following DNA sequences (SEQ ID NO's. 21–24, respectively):

B. subtilis 5'-AATCAAGCTTTATTTGATTTTAATGGACACCCGCTGCCTTCC-3'

B. licheniformis 5'-AATCAGGCATTGTTTGATTTTAAAGGACGTCCATTGCCGTCG-3'

B. agaradhaerens 5'-AACCAAACATTGTTTGATTTTGACGGTAATGCCTTACCATCA-3'

B. circulans 5'-AACCTGACGATGTTTGACTTCAAGGGCCAGAAGTTGCAATCG-3' and the following consensus primer (SEQ ID NO.25)

5'-A(T/C)C(T/A)(G/A)(G/A)CN(T/A)T(A/G)TTTGA(T/C)TT(T/C)(A/G)ANGGN(C/A) (A/G)NN(C/A)N(C/T)T(G/A)C(C/A)NTCN-3'

3) Motif characterizing all *Bacillus galactanases*:

S-Y-Y-P-x-W-H-G (SEQ ID NO.3)

with the following DNA sequences (SEQ ID NO's. 26–29, respectively)

B. subtilis 5'-TCCTATTATCCTTTCTGGCATGGC-3'

B. licheniformis 5'-TCGTATTATCCGTTTTGGCATGGC-3'

B. agaradhaerens 5'-TCGTATTATCCTTATTGGCATGGC-3'

B. circulans 5'-TCTTATTATCCCTGGTGGCATGGA-3' and the following consensus primer (SEQ ID NO.30):

5'-TCNTATTATCCNTNNTGGCATGG(C/A)-3'

4) Motif characterizing *B. subtilis* and *B. licheniformis*:

YD(S/A)NGNGYGG (SEQ ID NO.4)

with the following DNA sequences (SEQ ID NO's. 31–32, respectively):

B. subtilis 5'-TATGATTCAAATGGCAACGGGTATGGC-3'

B. licheniformis 5'-TATGATGCCAACGGCAACGGCTACGGA-3' and the following consensus primer (SEQ ID NO.33):

5'-TATGAT(T/G)C(A/C)AA(T/C)GGCAACGG(G/C)TA(T/C)GG(A/C)-3'

5) Motif characterizing *B. subtilis* and *B. licheniformis*:

VGP(K/A)(T/H)(Q/R)(I/L)EKNK(V/A)LWETYGSGWA(S/T)-SYAAEYDPEDAGKW(Y/F)GGSAV (SEQ ID NO.5)

with the following DNA sequences (SEQ ID NO's. 34–35, respectively):

*B. subtil433 is:*

5'-GTCGGGCCGAAGACACAGATA-GAGAAAAACAAAGTGTTATGGGAAACAT-ACGGGTCAGG GTGGGCGTCCAGCTATGCTGCT-GAATACGACCCTGAAGACGCCGGGAAGTGGTATGGGG GAAGTGCTGTA-3'

*B. licheniformis:*

5'-GTAGGACCGGCTCACCGGCTC-GAGAAAAATAAAGCGCTTTGGGAGACATACGGATCAGG CTGGGCTACAAGCTGCTGAATATGAC-CCGGAAGACGCAGGAAAGTGGTTTGGCG-GCAGCGCCGTA-3' and the following consensus primer (SEQ ID NO.36):

5'GT(A/C)GG(A/G)CCG(A/G)(A/C)(G/T)(A/C)(A/C)(A/C)C(A/G)G(A/C)T(A/C)GAGAAAAA (C/T)AAAG(T/C)G(T/C)T(A/T)TGGGA(A/G)ACATACGG(A/G)TCAGGCTGGGC(G/T)(A/T)C(C/A) GCTATGCTGCTGAATA(C/T)GACCC(G/T)GAAGACGC(A/C)GG(A/G)AAGTGGT(A/T)TGG(G/C)GG(A C)AG(T/C)GC(T/C)GTA-3'

6) Motif characterizing B. subtilis and B. licheniformis:

GG(F/L)AGETD    (SEQ ID NO6)

with the following DNA sequences (SEQ ID NO's. 37–38, respectively):

B. subtilis      5'-GGAGGATTTGCCGGTGAGACTGAT-3'

B. licheniformis 5'-GGGGGCCTTGCCGGTGAAACGGAT-3' and the following consensus primer (SEQ ID NO39):

5'-GG(A/C)GG(A/C)(T/C)TTGCCGGTGA(A/G)AC(T/G)GAT-3'

The DNA sequences shown above can be used either in their entire length or in the form of a subsequence thereof as a probe for similar sequences from these or other microorganisms. For those DNA sequences indicated above that are more than about 20 nucleotide sequences long, it will often be preferred to use probes comprising a unique portion of either such sequences, e.g. a subsequence comprising about 14 or more nucleotides, such as 16 or more nucleotides, typically about 18 or more nucleotides, e.g. about 20 nucleotides.

The four Bacillus galactanase amino acid sequences indicated above are shown in the attached FIG. 1 which also contains unique consensus regions which make them different from other known galactanases.

The four Bacillus galactanase DNA sequences are shown in SEQ ID NO's.7, 9, 11, and 13; and the encoded galactanase amino acid sequences are shown in SEQ ID NO's.8, 10, 12, and 14.

Using a Sequence of the Invention to Obtain Other Related Sequences

The disclosed sequence information herei n relating to polynucleotide sequences encoding galactanases of the invention can be used as a tool to identify other homnologous galactanase sequences. For instance, PCR (polymerase chain reaction) can be used to amplify sequences encoding other homologous galactanases from a variety of other microbial sources of in particular, but not limited to, different Bacillus species. As primers in the PCR reactions, DNA oligonucleotides consisting of, e.g., 16 or more bases of the above listed primers can be used, either in combination with another primer related to the ssequences of the invention, or in combination with any other primer useful for amplifying a PCR fragment.

Assay for Activity

A polypeptide of the invention having galactanase activity may be assayed for galactanase activity according to standard assay procedures known in the art, such as by applying a solution to be tested to 4 mm diameter holes punched out in agar plates containing 0.2% AZCL galactan (Megazyme, Australia).

Polynucleo tetides

Species homologues of a polypeptide of the invention having galactanase activity can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. DNA encoding an polypeptide of the invention having galactanase activity can then be isolated by a variety of methods, such as by probing with a complete or partial DNA or with one or more sets of degenerate probes based on the disclosed sequences. DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the galactanase cloned from B. licheniformis ATCC 14580 expressed and purified as described in examples, or by an activity test relating to a polypeptide having galactanase activity. Similar techniques can also be applied to the isolation of genomic clones.

Within preferred embodiments of the invention an isolated polynucleotide of the invention will hybridize to similar sized regions of SEQ ID No.7, SEQ ID No.40, SEQ ID No.41, SEQ ID No.42, SEQ No.43 or SEQ ID No.44, or a sequence complementary thereto, under at least medium stringency conditions.

In particular polynucleotides of the invention will hybridize to a double-stranded DNA probe comprising the sequence shown in: positions 1–2000 in SEQ ID NO.7 or positions 1–187 in SEQ ID No.40 or positions 1–61 in SEQ ID No.41 or positions 1–214 in SEQ ID No.42 or positions 1–107 in SEQ No.43 or positions 1–35 in Seq ID No.44 or to one of the other DNA sequences listed above, under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity >1×10⁹ cpm/µg ) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interes can be cloned in Gene Banks or DNA libraries by means of methods known in the art.

Polynucleotides encoding polypeptides having galactanase activity of the invention are then identified and isolated by, for example, hybridization or PCR.

The present invention further provides counterpart polypeptides and polynucleotides from different bacterial strains (orthologs or paralogs). Of particular interest are galactanase polypeptides from Gram-positive strains, including species of Bacillus such as Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, or in particular Bacillus licheniformis.

Polypeptides

Suitable galactanase polypeptides for purposes of the present invention are those that are substantially homologous to the polypeptides identified above and their species homologues (paralogs or orthologs). The term "substantially homologous" is used herein to denote polypeptides having at least 70%, preferably at least 80%, more preferably at least 85%, and even more preferably at least 90%, sequence identity to the sequences shown herein or their orthologs or paralogs. Such polypeptides will more preferably be at least 95% identical, and most preferably 98% or more identical to such sequences or their orthologs or paralogs. Percent sequence identity may be determined by conventional methods, e.g. the "align" program discussed above.

The sequence of amino acids no. 1–399 of SEQ ID No.8 is a mature galactanase sequence. The present invention also provides galactanase polypeptides that are substantially homologous to the polypeptides of SEQ ID NO.8 and their species homologs (paralogs or orthologs).

Substantially homologous proteins and polypeptides are characterized as having one or more amino acid substitutions, deletions or additions. These changes are preferably of a minor nature, that is conservative amino acid substitutions (see Table 1) and other substitutions that do not significantly affect the folding or activity of the protein or polypeptide; small deletions, typically of from one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See in general Ford et al., *Protein Expression and Purification* 2: 95–107, 1991, which is incorporated herein by reference. DNAs encoding affinity tags are available from commercial suppliers (e.g. Amersham Pharmacia, Piscataway, N.J., USA; New England Biolabs, Beverly, Mass., USA).

However, even though the changes described above preferably are of a minor nature, such changes may also be of a more substantial nature such as fusion of larger polypeptides of up to 300 amino acids or more as amino- or carboxyl-terminal extensions to a galactanase polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |

TABLE 1-continued

Conservative amino acid substitutions

| | |
|---|---|
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and/or unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the galactanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity i.e galactanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:1899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO 95/17413, or WO 95/22625. Briefly, these authors disclose methods for simultaneously randomizing two or more positions in a polypeptide, or recombination/shuffling of different mutations (WO 95/17413, WO 95/22625), followed by selecting for a functional polypeptide, and then sequencing the mutated polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to those disclosed herein and retain the galactanase activity of the wild-type protein.

Protein Production

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus Bacillus are especially preferred, such as *B. subtilis, B. lentus, B. brevis, B. stearothermophilus, B. alkalophilus, B. amyloliquefaciens, B. coagulans, B. circulans, B. lautus, B. thuringiensis, B. agaradhaerens, B. pumilus* and *B. licheniformis*.

Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989; Ausubel et al. (eds.), *Current Protocols in Molecular Biology*, John Wiley and Sons, Inc., NY, 1987; and *Bacillus subtilis and Other Gram-Positive Bacteria*, Sonensheim et al., 1993, American Society for Microbiology, Washington D.C.; which are incorporated herein by reference.

In general, a DNA sequence encoding a galactanase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design for those of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide or may be derived from another secreted protein or synthesized de novo. Numerous suitable secretory signal sequences are known in the art and reference is made to the following for further description of suitable secretory signal sequences, especially for secretion in a Bacillus host cell: Sonensheim et al., 1993; and Cutting, S. M.(eds.) *"Molecular Biological Methods for Bacillus"*, John Wiley and Sons, 1990. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum as required. The growth medium will generally select for cells containing the exogenously added DNA by, for example, drug selection or deficiency in an essential nutrient which is complemented by the selectable marker carried on the expression vector or cotransfected into the host cell.

Protein Isolation

When the expressed recombinant polypeptide is secreted, the polypeptide may be purified from the growth media. Preferably, the expression host cells are removed from the media before purification of the polypeptide (e.g. by centrifugation).

When the expressed recombinant polypeptide is not secreted from the host cell, the host cell is preferably disrupted and the polypeptide released into an aqueous "extract" which is the first stage of such purification techniques. Preferably, the expression host cells are removed from the media before the cell disruption, e.g. by centrifugation.

The cell disruption may be performed by conventional techniques such as by lysozyme digestion or by forcing the cells through high pressure. See e.g. Robert K. Scobes, Protein Purification, Second edition, Springer-Verlag, for further description of such cell disruption techniques.

Regardless of whether the expressed recombinant polypeptides (or chimeric polypeptides) are secreted or not, they can be purified using fractionation and/or conventional purification on chromatographic media.

Fractionation can be achieved by precipitation of the polypeptides with e.g. ammonium sulfate, organic solvents, PEG (polyethylene glycol) or PEI (polyethyleneimine) or by a selective denaturaturation of impurities, e.g. by adjusting pH and/or temperature.

Purification by liquid chromatography may include hydroxyapatite chromatography, size exclusion chromatography, ion-exchange chromatography, hydrophobic interaction chomatography and/or affinity chromatography. Chromatography media consists of a hydrophilic insoluble matrix (or support) to which ligands are attached (except size exclusion media, where no ligands are attached). Suitable matrixes include: agarose, cellulose, dextran, polyacrylamide, polystyrene, methacrylate, controlled pore glass, silica based resins, and the like. Often the matrixes are crosslinked to reduce their resistance to flow and in some cases the surface of the matrices is derivatized or coated with a hydrophilic polymer to avoid unspecific binding of biomolecules to the matrixes. Anion exchange media are derivatized with cationic ligands: PEI, DEAE, QAE or Q, such as DEAE sepharose FF (Amersham Pharmacia Biotech), cation exchange media with anionic ligands: CM, SP or S, such as SP sepharose FF (Amersham Pharmacia Biotech), and hydrophobic interaction media with hydrophobic ligands: phenyl, butyl, isopropyl or octyl groups, such as Toyopearl butyl 650 (TosoHaas). The matrices may also be modified with reactive groups that allow attachment of proteins (or other types of ligands) thought their amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activiation, hydrazide activation, and carboxyl and amino derivatives for carbodiimide coupling chemistries. Selection of a particular method for attachment is a matter of routine design and is determined in part by the properties of the chosen support and in part by the properties of the immobilized protein (or ligand). See, for example, *Affinity Chromatography: Principles & Methods*, Pharmacia LKB Biotechnology, Uppsala, Sweden, 1988.

Chromatographic media are well known and widely used in the art, and are available from a range of commercial suppliers.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant galactanase, but which microorganism simultaneously produces other enzymes, e.g. galactanases, proteases, or cellulases, being naturally occurring fermentation products of the microorganism, i.e. the enzyme complex conventionally produced by the corresponding naturally occurring microorganism.

The galactanase preparation of the invention may further comprise one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, pectin lyases, pectate lyases, pectin methylesterases, cellobiohydrolases, transglutaminases; or mixtures thereof. In a preferred embodiment, one or more of the enzymes in the preparation is produced by using recombinant techniques, i.e. the enzyme is a mono-component enzyme which is mixed with at least one other enzyme to form an enzyme preparation with the desired enzyme blend.

The enzymes used according to the invention may be produced by culturing a microorganism capable of producing the galactanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the galactanase enzyme. The growth medium may contain a conventional N-source such as peptone, yeast extract or casamino acids, a reduced amount of a conventional C-source such as dextrose or sucrose, and an inducer such as xyloglucan or composite plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, optionally followed by further purification e.g. as described in EP 0 406 314 or by crystallization as described in WO 97/15660.

Animal Feed Additive

As indicated above, the galactanases of the present invention are particularly suited for use as an animal feed additive for modification of the animal feed. The effect of the galactanases can be exerted either in vitro (by modifying components of the feed) or in vivo. The galactanases are particularly suited for addition to animal feed compositions containing high amounts of arabinogalactans or galactans, e.g. feed containing plant material from soy bean, rape seed, lupin etc. When added to the feed, the galactanase significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example, the indigestible galactan is degraded by galactanase, e.g. in combination with β-galactosidase, to galactose or galactooligomers which are digestible by the animal and thus contribute to the available energy of the feed. Also, by degrading galactan, the galactanase may improve the digestibility and uptake of non-carbohydrate feed constituents such as protein, fat and minerals.

We anticipate that the method of using a galactanase of the invention as an animal feed additive may be improved by further adding one or more enzymes selected from the group consisting of proteases, cellulases (endoglucanases), β-glucanases, hemicellulases, lipases, peroxidases, laccases, α-amylases, glucoamylases, cutinases, pectinases, reductases, oxidases, phenoloxidases, ligninases, pullulanases, arabinosidases, mannanases, xyloglucanases, xylanases, pectin acetyl esterases, polygalacturonases, rhamnogalacturonases, pectin lyases, pectate lyases, pectin methylesterases, cellobiohydrolases, transglutaminases; or mixtures thereof.

Additional uses for the galactanases of the invention include the following.

Degradation or Modification of Plant Material

The galactanases according to the invention may be used as an agent for degradation or modification of plant cell walls or any galactan-containing material originating from plant cells walls due to the high plant cell wall degrading activity of the enzymes.

The degradation of galactan by galactanases is facilitated by full or partial removal of the sidebranches. Arabinose sidegroups can be removed by a mild acid treatment or by alpha-arabinosidases.

The oligomers with are released by the galactanase or by a combination of galactanases and sidebranch-hydrolysing enzymes as mentioned above can be further degraded to free galactose by beta-galactosidases.

The galactanase of the present invention can be used without other pectinolytic or hemicellulytic enzymes or with limited activity of other pectinolytic or hemicellulytic enzymes to degrade galactans for production of oligosaccharides. The oligosaccharides may be used as bulking agents, like arabinogalactan oligosaccharides released from soy cell wall material, or of more or less purified arabinogalactans from plant material.

The galactanases of the present invention can be used in combination with other pectinolytic or hemicellulytic enzymes to degrade galactans to galactose and other monosaccharides.

The galactanase of the present invention may be used alone or together with other enzymes like glucanases, pectinases and/or hemicellulases to improve the extraction of oil from oilrich plant material, like soy-bean oil from soybeans, olive-oil from olives or rapeseed-oil from rape-seed or sunflower oil from sunflower.

The galactanases of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The galactanases of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other components than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearance has been shown to be a product of the actual combination of enzymes used for processing, i.e. the specificity of the enzymes with which the galactanase of the invention is combined. Examples include the production of clear juice e.g. from apples, pears or berries; cloud stable juice e.g. from apples, pears, berries, citrus or tomatoes; and purees e.g. from carrots and tomatoes.

The galactanases of the invention may be used in modifying the viscosity of plant cell wall derived material. For instance, the galactanase may be used to reduce the viscosity of feed which contain galactan and to promote processing of viscous galactan containing material. The viscosity reduction may be obtained by treating the galactan containing plant material with an enzyme preparation of the invention under suitable conditions for full or partial degradation of the galactan containing material The galactanases can be used e.g. in combination with other enzymes for the removal of pectic substances from plant fibres. This removal is essential e.g. in the production of textile fibres or other cellulosic materials. For this purpose plant fibre material is treated with a suitable amount of the galactanase of the invention under suitable conditions for obtaining full or partial degradation of pectic substances associated with the plant fibre material.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

Use in the Detergent Industry

In further aspects, the present invention relates to a detergent composition comprising the galactanases or galactanase preparation of the invention, and to a process for machine treatment of fabrics comprising treating fabric during a washing cycle of a machine washing process with a washing solution containing the galactanase or galactanase preparation of the invention.

Typically, the detergent composition of the invention comprises conventional ingredients such as surfactants (anionic, nonionic, zwitterionic, amphoteric), builders, and other ingredients, e.g. as described in WO 97/01629 which is hereby incorporated by reference.

Use in the Textile and Cellulosic Fiber Processing Industries

The galactanases of the present invention can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in s preparation are desizing (for woven goods), scouring and bleaching. A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the nonspecific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

It is contemplated that the scouring step can be carried out using the galactanase or galactanase preparation of the present invention in combination with a few other enzyme activities at a temperature of about 500° C.–80° C. and a pH of about 7–11, thus substituting or supplementing the highly causticizing agents.

The invention will be further illustrated by the following non-limiting examples.

Determination of Catalytic Activity of Galactanase (GalU)

The substrate galactan was obtained from Megazyme, Australia (arabinofuranosidase pretreated with more than 91% galactose, 2% arabinose, 1.7% rhamnose and 3.5% xylose).

Incubation conditions: 0.9% substrate in 0.1 M phosphate, pH 7.5, at 40° C. for 20 min.

The formation of reducing sugars is determined by using -phydroxy-benzoic-acid-hydrazide (PHBAH) modified from Lever (Lever M., 1972, A new reaction for colormetric determination of carbohydrates. Anal. Biochem. 47:273–279) using 5 gram of potassium sodium tartrate in addition to 1.5 gram of PHBAH. Glucose is used as reference for determination of the reducing groups.

One GalU is equivalent to the formation of 1 $\mu$mol reducing sugar per min.

Materials and Methods

Strains

*Bacillus licheniformis* ATCC 14580.

*B. subtilis* PL2306. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315–4321) disrupted in the transcriptional unit of the known Bacillus subtilis cellulase gene, resulting in cellulase negative cells. The disruption was performed essentially as described in ( Eds. A. L. Sonenshein, J. A. Hoch and Richard Losick (1993) *Bacillus subtilis* and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

Plasmids pMOL944: This plasmid is a pUB110 derivative essentially containing elements making the plasmid propagatable in *Bacillus subtilis*, kanamycin resistance gene and having a strong promoter and signal peptide cloned from the amyL gene of *B.licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944: The pUB110 plasmid (McKenzie, T. et al., 1986, Plasmid 15:93–103) was digested with the unique restriction enzyme NciI . A PCR fragment amplified from the amyL promoter encoded on the plasmid pDN1981 (P. L. Jørgensen et al.,1990, Gene, 96, p37–41.) was digested with NciI and inserted in the NciI digested pUB110 to give the plasmid pSJ2624.

The two PCR primers used have the following sequences:

LWN5494 (SEQ ID NO.45) 5'-GTCGCCGGGGCGGCCGC-TATCAATTGGTAACTGTATCTCAGC -3'

LWN5495 (SEQ ID NO.46) 5'-GTCGCCCGGGAGCTCTGAT-CAGGTACCAAGCTTGTCGACCTGCAGA ATGAGGCAG-CAAGAAGAT -3'

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 (SEQ ID NO.47) 5'-GTCGGCGGCCGCTGATCACG-TACCAAGCTTGT-CGACCTGCAGAATGAGGCAGCAA-GAAGAT-3'

LWN5939 (SEQ ID NO.48) 5'-GTCGGAGCTCTATCAATTGG-TAACTGTATCTCAGC-3'

The plasmid pSJ2670 was digested with the restriction enzymes PstI and BclI and a PCR fragment amplified from a cloned DNA sequence encoding the alkaline amylase SP722 (disclosed in WO95/26397) was digested with PstI and BclI and inserted to give the plasmid pMOL944. The two primers used for PCR amplification have the following sequence:

LWN7864 (SEQ ID NO.49) 5'-AACAGCTGATCACGACT-GATCTTTTAGCTTGGCAC-3'

LWN7901 (SEQ ID NO.50) 5'-AACTGCAGCCGCGGCACAT-CATAATGGGACAAATGGG-3'

The primer #LWN7901 inserts a SacII site in the plasmid.

Genomic DNA Preparation

The strain *Bacillus licheniformis* ATCC 14580 was propagated in liquid medium 3 as specified by ATCC (American Type Culture Collection, USA). After 18 hours incubation at 37° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

The galactanase encoding DNA sequence of the invention was PCR amplified using the PCR primer set consisting of these two oligo nucleotides:

Galactanase.B.lich.upper.SacII     (SEQ ID NO.51):

5'-TCT GCA G<u>CC GCG G</u>CA CAC AGA GAT TCA GGC ACG GC-3'

Galactanase.E.lich.lower.NotI     (SEQ ID NO.52):

5'GCG TTG AGA A<u>GC GGC CGC</u>CGG CCT TTT TTC CAT TCT GC-3'

Restriction sites SacII and NotII are underlined.

Chromosomal DNA isolated from *B.licheniformis* ATCC 14580 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1.3 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 1OmM Tris-HCl, pH 8.5.

5 µg of pMOL944 and twentyfive-µl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B.subtilis* PL2306. The transformed cells were plated onto LBPG-10 μg/ml of Kanamycin –0.1% AZCL-Galactan-agar plates. After 18 hours incubation at 37° C. cells positively expressing the cloned Galactanase were seen as colonies surrounded by large blue halos. One such positive clone was restreaked several times on agar plates as used above, this clone was called MB547. The clone MB547 was gown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B.subtilis* plasmid preparations. This plasmid DNA was used as template for DNA sequencing.

The DNA corresponding to the mature part of the galactanase was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The sequence corresponds to the DNA sequence shown in SEQ ID NO.38.

Media

TY (as described in Ausubel, F. M. et al. (eds.) "Current protocols in Molecular Biology". John Wiley and Sons, 1995).
LB agar (as described in Ausubel, F. M. et al. (eds.) "Current protocols in Molecular Biology". John Wiley and Sons, 1995).
LBPG is LB agar supplemented with 0.5% Glucose and 0.05 M potassium phosphate, pH 7.0
AZCL-HE-Galactan is added to LBPG-agar to 0.5% AZCL-HE-cellulose is from Megazyme, Australia.
BPX media is described in EP 0 506 780 (WO 91/09129).

EXAMPLE 1

Expression and Purification of Galactanase from Bacillus licheniformis

The clone MB547 (cf. Materials and Methods) was grown in 25×200 ml BPX media with 10 μg/ml of Kanamycin in 500 ml two baffled shakeflasks for 5 days at 37° C. at 300 rpm.

3000 ml shake flask culture fluid of the clone MB 547 batch #9805 was diluted with 2000 ml of water and pH adjusted to 7.5. 200 ml of cationic agent (C521) and 200 ml of anionic agent (A130) was added during agitation for flocculation. The flocculated material was separated by centrifugation using a Sorval RC 3B centrifuge at 10000 rpm for 30 min at 6° C. The resulting supernatant contained 308 GalU per ml in a total volume of 5000 ml.

The supernatant was clarified using a Whatman glass filters GF/D and C and finally concentrated on a filtron with a cut off of 10 kDa.

1200 ml concentrate contained 1080 GalU per ml (yield 84%) 600 ml of this concentrate was adjusted to pH 5.0 using acetic acid and the precipitate discarded. The clear solutions was applied to cat-ionexchange chromatography using a 300 ml S-Sepharose column equilibrated with 50 mmol Sodium acetate pH 5.0. The galactanase activity bound and was eluted using a sodium chloride gradient.

The pure enzyme gave a single band in SDS-PAGE with a molecular weight of 45 kDa.

The amino acid sequence of the galactanase enzyme, i.e. the translated DNA sequence, is shown in SEQ ID NO.8.

EXAMPLE 2

Characterization of Galactanase from *Bacillus Licheniformis*

The temperature optimum of the galactanase produced according to example 1 was found to be 50° C. at pH 7.5.

The molar extinction coefficient based on amino acid composition was 88190.

Determination of galactanase activity: GalU it is measured at pH 7.5 using 0.1 M phosphate buffer and 1% substrate (Galactan high purity from Lupin) sold by Megazyme. Incubation 20 min at 40° C. One unit is equivalent to the formation of 1 μmol reducing sugar per min.

Kinetic determination of the purified galactanase using different concentration of galactan from Megazyme. 10 different concentration of galactan between 0.06 gram per 1 to 15 gram per 1 in 0.1 M phosphate buffer pH 7.5. The galactanase was incubated with highly purified galactan in duplicate for 20 min. The formation of reducing sugars was determined as described in example 3.

Kcat of 2.1 per sec was calculated and Km of 2 gram per 1 of galactan was determined.

EXAMPLE 3

Application of the Galactanase Enzyme from *B. licheniformis* in Detergent

Application in detergents of the enzyme produced according to example 1 was done as follows:

The substrate 2% was Galactan (Lupin) from Megazyme. Substrate 0.5 ml and 0.5 ml buffer or 2× concentrated detergent were mixed and temperature adjusted to 40° C., then 0.1 ml enzyme diluted in water was added and pre-incubated for 5 minutes. Duplicate samples were incubated for 20 min and background samples were stopped with 0.5 ml NaOH before adding the enzyme. Then the sample was diluted 11 fold in 0.5 M NaOH and PHAB reagent was added, then the sample was cooked for 10 min and the formation of yellow colour determined at 410 nm using a spectrophotometer used for determination of reducing sugars using standard procedures.

A glucose standard was used for calibration.

Detergents (all commercial products available from The Procter & Gamble Company):
  a. US detergent US Tide 1 g/l in 9 German hardness grain per 1 water
  b. Ariel Color powder 5 gram/l in 18 German hardness grain per 1 water
  c. Ariel Color liquid 5 gram/l in 18 German hardness grain per 1 water Buffers

| | |
|---|---|
| pH 7.5 | 0.1M Phosphate |
| pH 10.0 | 0.1M Glycine |

| | |
|---|---|
| Buffer pH 7.5 | 255 |
| Ariel color liquid | 239 |
| Ariel color powder | 99 |
| Tide Powder | 188 |
| Buffer pH 10 | 56 |

Results (Data are formation of μmol reducing sugars per mg of protein):

The results indicate that the galactanase of the invention is very active in the presence of detergent component and therefore well suited to be used as a cleaning agent, for example in detergents.

What is claimed is:

1. An isolated polynucleotide molecule encoding a polypeptide having galactanase activity selected from the group consisting of:
   a) polynucleotide molecules comprising a nucleotide sequence as shown in SEQ ID NO.11;
   b) polynucleotide molecules that encode a polypeptide that is at least 70% identical to the amino acid sequence as shown in SEQ ID NO.12; and
   c) degenerate nucleotide sequences of (a) or (b).

2. The isolated polynucleotide molecule according to claim 1, wherein the polynucleotide is DNA.

3. An isolated polynucleotide molecule encoding a polypeptide having galactanase activity selected from the group consisting of:
   a) polynucleotide molecules comprising a nucleotide sequence as shown in SEQ ID NO.7;
   b) polynucleotide molecules that encode a polypeptide that is at least 85% identical to the amino acid sequence as shown in SEQ ID NO.8; and
   c) degenerate nucleotide sequences of (a) or (b).

4. The isolated polynucleotide molecule according to claim 3, wherein the polynucleotide is DNA.

5. An expression vector comprising a polynucleotide sequence as defined in claim 1.

6. A cell into which has been introduced an expression vector according to claim 5, wherein the cell expresses the polypeptide encoded by the polynucleotide sequence.

7. A method of producing a polypeptide having galactanase activity comprising culturing a cell into which has been introduced an expression vector according to claim 5, whereby the cell expresses a polypeptide encoded by the DNA segment; and recovering the polypeptide.

\* \* \* \* \*

SEQUENCE LISTING

```
<160> NUMBER OF SEQ ID NOS: 52

<210> SEQ ID NO 1
<211> LENGTH: 10
<212> TYPE: PRT
<213> ORGANISM: Bacillus
<220> FEATURE:
<221> NAME/KEY: SIMILAR
<222> LOCATION: (1)..(10)
<223> OTHER INFORMATION: Conserved region of Bacillus galactanases
<220> FEATURE:
<223> OTHER INFORMATION: Xaa at position 2,3,5,7,8 is any amino acid

<400> SEQUENCE: 1

Tyr Xaa Xaa Thr Xaa Glu Xaa Xaa Asp Gly
 1               5                   10

<210> SEQ ID NO 2
<211> LENGTH: 14
<212> TYPE: PRT
<213> ORGANISM: Bacillus
<220> FEATURE:
<221> NAME/KEY: SIMILAR
<222> LOCATION: (1)..(14)
<223> OTHER INFORMATION: Conserved region of Bacillus galactanases
<220> FEATURE:
<223> OTHER INFORMATION: Position 4 in this conserved region is either
      Methionine (M) or Leucine (L)
<220> FEATURE:
<223> OTHER INFORMATION: Xaa at position 2,3,4,8,10,11,13 is any amino
      acid

<400> SEQUENCE: 2

Asn Xaa Xaa Xaa Phe Asp Phe Xaa Gly Xaa Xaa Leu Xaa Ser
 1               5                   10

<210> SEQ ID NO 3
<211> LENGTH: 8
<212> TYPE: PRT
<213> ORGANISM: Bacillus
<220> FEATURE:
<221> NAME/KEY: SIMILAR
<222> LOCATION: (1)..(8)
<223> OTHER INFORMATION: Conserved region of Bacillus galactanases
<220> FEATURE:
<223> OTHER INFORMATION: Xaa at position 5 is any amino acid

<400> SEQUENCE: 3

Ser Tyr Tyr Pro Xaa Trp His Gly
 1               5

<210> SEQ ID NO 4
<211> LENGTH: 10
<212> TYPE: PRT
```

-continued

```
<213> ORGANISM: Bacillus
<220> FEATURE:
<221> NAME/KEY: SIMILAR
<222> LOCATION: (1)..(10)
<223> OTHER INFORMATION: Conserved region of Bacillus galactanases
<220> FEATURE:
<223> OTHER INFORMATION: Position 3 in this conserved region is either
      Serine (S) or Alanine (A)
<220> FEATURE:
<223> OTHER INFORMATION: Xaa at position 3 is any amino acid

<400> SEQUENCE: 4

Tyr Asp Xaa Asn Gly Asn Gly Tyr Gly Gly
  1               5                   10

<210> SEQ ID NO 5
<211> LENGTH: 43
<212> TYPE: PRT
<213> ORGANISM: Bacillus
<220> FEATURE:
<221> NAME/KEY: SIMILAR
<222> LOCATION: (1)..(43)
<223> OTHER INFORMATION: Conserved region of Bacillus galactanases.
<220> FEATURE:
<223> OTHER INFORMATION: Position 4 in this conserved region is either
      Lysine (K) or Alanine (A).
<220> FEATURE:
<223> OTHER INFORMATION: Position 5 is either Threonine (T) or Histidine
      (H).
<220> FEATURE:
<223> OTHER INFORMATION: Position 6 is either Glutamine (Q) or Arginine
      (R).
<220> FEATURE:
<223> OTHER INFORMATION: Position 7 is either Isoleucine (I) or Leucine
      (L).
<220> FEATURE:
<223> OTHER INFORMATION: Position 12 is either Valine (V) or Alanine
      (A).
<220> FEATURE:
<223> OTHER INFORMATION: Position 23 is either Serine (S) or Threonine
      (T).
<220> FEATURE:
<223> OTHER INFORMATION: Position 38 is either Tyrosine (Y) or
      Phenylalanine (F)
<220> FEATURE:
<223> OTHER INFORMATION: Xaa at position 4,5,6,7,12,23,38 is any amino
      acid

<400> SEQUENCE: 5

Val Gly Pro Xaa Xaa Xaa Xaa Glu Lys Asn Lys Xaa Leu Trp Glu Thr
  1               5                   10                  15

Tyr Gly Ser Gly Trp Ala Xaa Ser Tyr Ala Ala Glu Tyr Asp Pro Glu
             20                  25                  30

Asp Ala Gly Lys Trp Xaa Gly Gly Ser Ala Val
         35                  40

<210> SEQ ID NO 6
<211> LENGTH: 8
<212> TYPE: PRT
<213> ORGANISM: Bacillus
<220> FEATURE:
<221> NAME/KEY: SIMILAR
<222> LOCATION: (1)..(8)
<223> OTHER INFORMATION: Conserved region of Bacillus galactanases.
<220> FEATURE:
<223> OTHER INFORMATION: Position 3 in this conserved region is either
      Phenylalanine (F) or Leucine (L)
<220> FEATURE:
<223> OTHER INFORMATION: Xaa at position 3 is any amino acid

<400> SEQUENCE: 6

Gly Gly Xaa Ala Gly Glu Thr Asp
```

<210> SEQ ID NO 7
<211> LENGTH: 1200
<212> TYPE: DNA
<213> ORGANISM: Bacillus licheniformis ATCC 14580
<220> FEATURE:
<221> NAME/KEY: CDS
<222> LOCATION: (1)..(1197)
<223> OTHER INFORMATION: DNA encoding the Galactanase shown in SEQ ID NO.8.

<400> SEQUENCE: 7

| | | | | | | | | | | | | | | | | |
|---|---|---|---|---|---|---|---|---|---|---|---|---|---|---|---|---|
| gca | cac | aga | gat | tca | ggg | acg | gca | aaa | agc | ggc | ctt | tat | gtt | gaa | aag | 48 |
| Ala | His | Arg | Asp | Ser | Gly | Thr | Ala | Lys | Ser | Gly | Leu | Tyr | Val | Glu | Lys | |
| 1 | | | | 5 | | | | | 10 | | | | | 15 | | |
| gtt | tca | ggg | ctt | cgc | aag | gat | ttt | ata | aaa | ggg | gtt | gat | gtt | tcg | agc | 96 |
| Val | Ser | Gly | Leu | Arg | Lys | Asp | Phe | Ile | Lys | Gly | Val | Asp | Val | Ser | Ser | |
| | | | 20 | | | | | 25 | | | | | 30 | | | |
| atc | atc | gct | ttg | gaa | gag | agc | ggc | gtc | gcc | ttt | tac | aat | gaa | tcc | gga | 144 |
| Ile | Ile | Ala | Leu | Glu | Glu | Ser | Gly | Val | Ala | Phe | Tyr | Asn | Glu | Ser | Gly | |
| | | 35 | | | | | 40 | | | | | 45 | | | | |
| aag | aaa | cag | gat | ata | ttc | aac | acg | ctg | aag | gaa | gca | ggc | gtc | aat | tat | 192 |
| Lys | Lys | Gln | Asp | Ile | Phe | Asn | Thr | Leu | Lys | Glu | Ala | Gly | Val | Asn | Tyr | |
| | 50 | | | | | 55 | | | | | 60 | | | | | |
| gtc | cgg | gtg | cgc | ata | tgg | aat | gat | ccc | tat | gat | gcc | aac | ggc | aac | ggc | 240 |
| Val | Arg | Val | Arg | Ile | Trp | Asn | Asp | Pro | Tyr | Asp | Ala | Asn | Gly | Asn | Gly | |
| 65 | | | | | 70 | | | | | 75 | | | | | 80 | |
| tac | gga | ggg | ggc | aat | aat | gat | ctg | gaa | aaa | gcg | att | cag | atc | gga | aaa | 288 |
| Tyr | Gly | Gly | Gly | Asn | Asn | Asp | Leu | Glu | Lys | Ala | Ile | Gln | Ile | Gly | Lys | |
| | | | | 85 | | | | | 90 | | | | | 95 | | |
| cgg | gcc | aat | gcc | aac | gga | atg | aag | ctg | ctg | gcg | gat | ttc | cac | tat | tcc | 336 |
| Arg | Ala | Asn | Ala | Asn | Gly | Met | Lys | Leu | Leu | Ala | Asp | Phe | His | Tyr | Ser | |
| | | | 100 | | | | | 105 | | | | | 110 | | | |
| gat | ttc | tgg | gcg | gac | ccg | gcg | aaa | cag | aaa | gcg | ccg | aaa | gca | tgg | gcg | 384 |
| Asp | Phe | Trp | Ala | Asp | Pro | Ala | Lys | Gln | Lys | Ala | Pro | Lys | Ala | Trp | Ala | |
| | | 115 | | | | | 120 | | | | | 125 | | | | |
| aac | cta | aac | ttt | gaa | gat | aaa | aag | acg | gcg | ctt | tat | caa | tat | aca | aaa | 432 |
| Asn | Leu | Asn | Phe | Glu | Asp | Lys | Lys | Thr | Ala | Leu | Tyr | Gln | Tyr | Thr | Lys | |
| | 130 | | | | | 135 | | | | | 140 | | | | | |
| caa | agc | ctt | aaa | gcg | atg | aaa | gca | gcg | ggc | atc | gac | atc | ggc | atg | gtg | 480 |
| Gln | Ser | Leu | Lys | Ala | Met | Lys | Ala | Ala | Gly | Ile | Asp | Ile | Gly | Met | Val | |
| 145 | | | | | 150 | | | | | 155 | | | | | 160 | |
| cag | gtc | ggt | aac | gaa | aca | aac | ggg | ggc | ctt | gcc | ggt | gaa | acg | gat | tgg | 528 |
| Gln | Val | Gly | Asn | Glu | Thr | Asn | Gly | Gly | Leu | Ala | Gly | Glu | Thr | Asp | Trp | |
| | | | | 165 | | | | | 170 | | | | | 175 | | |
| gcg | aag | atg | agc | caa | tta | ttc | aac | gcc | ggg | agt | caa | gcg | gtg | cga | gag | 576 |
| Ala | Lys | Met | Ser | Gln | Leu | Phe | Asn | Ala | Gly | Ser | Gln | Ala | Val | Arg | Glu | |
| | | | 180 | | | | | 185 | | | | | 190 | | | |
| acg | gat | tcg | aat | atc | cta | gtc | gcc | ttg | cat | ttt | acc | aat | ccg | gag | acg | 624 |
| Thr | Asp | Ser | Asn | Ile | Leu | Val | Ala | Leu | His | Phe | Thr | Asn | Pro | Glu | Thr | |
| | | 195 | | | | | 200 | | | | | 205 | | | | |
| tca | gga | agg | tac | gct | tgg | att | gcc | gag | acg | ctt | cat | cgg | cat | cat | gta | 672 |
| Ser | Gly | Arg | Tyr | Ala | Trp | Ile | Ala | Glu | Thr | Leu | His | Arg | His | His | Val | |
| | 210 | | | | | 215 | | | | | 220 | | | | | |
| gac | tac | gat | gtg | ttt | gca | agc | tcg | tat | tat | ccg | ttt | tgg | cat | ggc | acg | 720 |
| Asp | Tyr | Asp | Val | Phe | Ala | Ser | Ser | Tyr | Tyr | Pro | Phe | Trp | His | Gly | Thr | |
| 225 | | | | | 230 | | | | | 235 | | | | | 240 | |
| ctg | aag | aat | tta | aca | tcc | gtc | ctg | aca | tct | gtc | gca | gat | acg | tac | ggc | 768 |
| Leu | Lys | Asn | Leu | Thr | Ser | Val | Leu | Thr | Ser | Val | Ala | Asp | Thr | Tyr | Gly | |
| | | | | 245 | | | | | 250 | | | | | 255 | | |

-continued

```
aaa aaa gtc atg gtt gct gag aca tct tat acg tat acg gct gaa gac      816
Lys Lys Val Met Val Ala Glu Thr Ser Tyr Thr Tyr Thr Ala Glu Asp
        260                 265                 270 gga gac gga cac gga aat aca gct ccg aaa aac ggc caa acg ctg aat      864
Gly Asp Gly His Gly Asn Thr Ala Pro Lys Asn Gly Gln Thr Leu Asn
            275                 280                 285 aat ccg gtc acc gtt caa ggg cag gcg aac gcg gtc cgt gat gtg att      912
Asn Pro Val Thr Val Gln Gly Gln Ala Asn Ala Val Arg Asp Val Ile
290                 295                 300 caa gcg gtc agc gac gta ggt gaa gcc gga atc ggc gtt ttc tat tgg      960
Gln Ala Val Ser Asp Val Gly Glu Ala Gly Ile Gly Val Phe Tyr Trp
305                 310                 315                 320 gaa ccg gca tgg att ccg gta gga ccg gct cac cgg ctc gag aaa aat     1008
Glu Pro Ala Trp Ile Pro Val Gly Pro Ala His Arg Leu Glu Lys Asn
                325                 330                 335 aaa gcg ctt tgg gag aca tac gga tca ggc tgg gct aca agc tat gct     1056
Lys Ala Leu Trp Glu Thr Tyr Gly Ser Gly Trp Ala Thr Ser Tyr Ala
            340                 345                 350 gct gaa tat gac ccg gaa gac gca gga aag tgg ttt ggc ggc agc gcc     1104
Ala Glu Tyr Asp Pro Glu Asp Ala Gly Lys Trp Phe Gly Gly Ser Ala
        355                 360                 365 gta gac aat cag gca ttg ttt gat ttt aaa gga cgt cca ttg ccg tcg     1152
Val Asp Asn Gln Ala Leu Phe Asp Phe Lys Gly Arg Pro Leu Pro Ser
370                 375                 380 ctt cat gtg ttt caa tat gtt gat acg gga aca cca ttc aaa aat tga     1200
Leu His Val Phe Gln Tyr Val Asp Thr Gly Thr Pro Phe Lys Asn
385                 390                 395
```

<210> SEQ ID NO 8
<211> LENGTH: 399
<212> TYPE: PRT
<213> ORGANISM: Bacillus licheniformis ATCC 14580

<400> SEQUENCE: 8

```
Ala His Arg Asp Ser Gly Thr Ala Lys Ser Gly Leu Tyr Val Glu Lys
  1               5                  10                  15

Val Ser Gly Leu Arg Lys Asp Phe Ile Lys Gly Val Asp Val Ser Ser
            20                  25                  30

Ile Ile Ala Leu Glu Glu Ser Gly Val Ala Phe Tyr Asn Glu Ser Gly
        35                  40                  45

Lys Lys Gln Asp Ile Phe Asn Thr Leu Lys Glu Ala Gly Val Asn Tyr
 50                  55                  60

Val Arg Val Arg Ile Trp Asn Asp Pro Tyr Asp Ala Asn Gly Asn Gly
 65                  70                  75                  80

Tyr Gly Gly Gly Asn Asn Asp Leu Glu Lys Ala Ile Gln Ile Gly Lys
                85                  90                  95

Arg Ala Asn Ala Asn Gly Met Lys Leu Leu Ala Asp Phe His Tyr Ser
           100                 105                 110

Asp Phe Trp Ala Asp Pro Ala Lys Gln Lys Ala Pro Lys Ala Trp Ala
       115                 120                 125

Asn Leu Asn Phe Glu Asp Lys Lys Thr Ala Leu Tyr Gln Tyr Thr Lys
   130                 135                 140

Gln Ser Leu Lys Ala Met Lys Ala Ala Gly Ile Asp Ile Gly Met Val
145                 150                 155                 160

Gln Val Gly Asn Glu Thr Asn Gly Gly Leu Ala Gly Glu Thr Asp Trp
               165                 170                 175

Ala Lys Met Ser Gln Leu Phe Asn Ala Gly Ser Gln Ala Val Arg Glu
           180                 185                 190
```

```
Thr Asp Ser Asn Ile Leu Val Ala Leu His Phe Thr Asn Pro Glu Thr
        195                 200                 205

Ser Gly Arg Tyr Ala Trp Ile Ala Glu Thr Leu His Arg His His Val
        210                 215                 220

Asp Tyr Asp Val Phe Ala Ser Ser Tyr Tyr Pro Phe Trp His Gly Thr
225                 230                 235                 240

Leu Lys Asn Leu Thr Ser Val Leu Thr Ser Val Ala Asp Thr Tyr Gly
                245                 250                 255

Lys Lys Val Met Val Ala Glu Thr Ser Tyr Thr Tyr Thr Ala Glu Asp
                260                 265                 270

Gly Asp Gly His Gly Asn Thr Ala Pro Lys Asn Gly Gln Thr Leu Asn
        275                 280                 285

Asn Pro Val Thr Val Gln Gly Gln Ala Asn Ala Val Arg Asp Val Ile
        290                 295                 300

Gln Ala Val Ser Asp Val Gly Glu Ala Gly Ile Gly Val Phe Tyr Trp
305                 310                 315                 320

Glu Pro Ala Trp Ile Pro Val Gly Pro Ala His Arg Leu Glu Lys Asn
                325                 330                 335

Lys Ala Leu Trp Glu Thr Tyr Gly Ser Gly Trp Ala Thr Ser Tyr Ala
                340                 345                 350

Ala Glu Tyr Asp Pro Glu Asp Ala Gly Lys Trp Phe Gly Gly Ser Ala
        355                 360                 365

Val Asp Asn Gln Ala Leu Phe Asp Phe Lys Gly Arg Pro Leu Pro Ser
        370                 375                 380

Leu His Val Phe Gln Tyr Val Asp Thr Gly Thr Pro Phe Lys Asn
385                 390                 395

<210> SEQ ID NO 9
<211> LENGTH: 756
<212> TYPE: DNA
<213> ORGANISM: Bacillus circulans
<220> FEATURE:
<221> NAME/KEY: CDS
<222> LOCATION: (1)..(756)
<223> OTHER INFORMATION: DNA encoding the Galactanase shown in SEQ ID
      NO.10.

<400> SEQUENCE: 9 att ctt gga atg gat gtg tca ttt atg gat gaa att gag cag gat gag      48
Ile Leu Gly Met Asp Val Ser Phe Met Asp Glu Ile Glu Gln Asp Glu
  1               5                  10                  15 aac ggg cag cag gaa gac ttg ctg acc ctt ctc aag att cgt ttg cgt      96
Asn Gly Gln Gln Glu Asp Leu Leu Thr Leu Leu Lys Ile Arg Leu Arg
                 20                  25                  30 ata tgg aac gac cct gta ggc gga ttc tgt gcg gtt gcc aaa cgg gtc     144
Ile Trp Asn Asp Pro Val Gly Gly Phe Cys Ala Val Ala Lys Arg Val
         35                  40                  45 aag gag cac ggc ctg cat ttc ttg gat cgc tgg gct gat cct gcc aat     192
Lys Glu His Gly Leu His Phe Leu Asp Arg Trp Ala Asp Pro Ala Asn
 50                  55                  60 caa tgg aag cca aag gcc gag gaa ttg caa cgt gcg gtg tgt aac tat     240
Gln Trp Lys Pro Lys Ala Glu Glu Leu Gln Arg Ala Val Cys Asn Tyr
 65                  70                  75                  80 acg gca gat gtg cat gat gcc ctg ccg gat atg gta cag gta ggg aat     288
Thr Ala Asp Val His Asp Ala Leu Pro Asp Met Val Gln Val Gly Asn
                 85                  90                  95 gaa att gat gaa ggg cga gtc agc gga gaa gaa cat gat acg gat gaa     336
Glu Ile Asp Glu Gly Arg Val Ser Gly Glu Glu His Asp Thr Asp Glu
```

```
                    100                     105                     110
ggg ctt gtg aag tat ggt att gct gca gtt aaa tcc gtt gat atc cat      384
Gly Leu Val Lys Tyr Gly Ile Ala Ala Val Lys Ser Val Asp Ile His
        115                     120                     125 att gac cgc ggc ggg gat aat gca gag agc cgc aag gcg ctt ggg gtg      432
Ile Asp Arg Gly Gly Asp Asn Ala Glu Ser Arg Lys Ala Leu Gly Val
130                     135                     140 gag ttt gat atc att gga ctc tct tat tat ctg gac gcg ttg cgg gac      480
Glu Phe Asp Ile Ile Gly Leu Ser Tyr Tyr Leu Asp Ala Leu Arg Asp
145                     150                     155                 160 aat ctg cac gac ttg gct gaa cgg gtt gtt gaa acg gct tat cct tgg      528
Asn Leu His Asp Leu Ala Glu Arg Val Val Glu Thr Ala Tyr Pro Trp
            165                     170                     175 aca ctg gag caa cct gat aat cag gaa gaa ttg ctg ttg cca ggg tat      576
Thr Leu Glu Gln Pro Asp Asn Gln Glu Glu Leu Leu Leu Pro Gly Tyr
                180                     185                     190 ccg gca agt gtg ctg aag gat ctg ctg caa att gtt cgt gaa gtt ccc      624
Pro Ala Ser Val Leu Lys Asp Leu Leu Gln Ile Val Arg Glu Val Pro
            195                     200                     205 ggc ggt tat tgg gag cct gcc tgg att cca agc aag gaa gaa tgg tct      672
Gly Gly Tyr Trp Glu Pro Ala Trp Ile Pro Ser Lys Glu Glu Trp Ser
210                     215                     220 tgg ggg aac ctg acg atg ttt gac ttc aag ggc cag aag ttg aag gcc      720
Trp Gly Asn Leu Thr Met Phe Asp Phe Lys Gly Gln Lys Leu Lys Ala
225                     230                     235                 240 gga ctg gaa aat gaa acg gaa tgg gat gag cag ccg                      756
Gly Leu Glu Asn Glu Thr Glu Trp Asp Glu Gln Pro
            245                     250

<210> SEQ ID NO 10
<211> LENGTH: 252
<212> TYPE: PRT
<213> ORGANISM: Bacillus circulans

<400> SEQUENCE: 10

Ile Leu Gly Met Asp Val Ser Phe Met Asp Glu Ile Glu Gln Asp Glu
 1               5                  10                  15

Asn Gly Gln Gln Glu Asp Leu Leu Thr Leu Leu Lys Ile Arg Leu Arg
            20                  25                  30

Ile Trp Asn Asp Pro Val Gly Gly Phe Cys Ala Val Ala Lys Arg Val
        35                  40                  45

Lys Glu His Gly Leu His Phe Leu Asp Arg Trp Ala Asp Pro Ala Asn
    50                  55                  60

Gln Trp Lys Pro Lys Ala Glu Glu Leu Gln Arg Ala Val Cys Asn Tyr
65                  70                  75                  80

Thr Ala Asp Val His Asp Ala Leu Pro Asp Met Val Gln Val Gly Asn
                85                  90                  95

Glu Ile Asp Glu Gly Arg Val Ser Gly Glu His Asp Thr Asp Glu
            100                 105                 110

Gly Leu Val Lys Tyr Gly Ile Ala Ala Val Lys Ser Val Asp Ile His
        115                 120                 125

Ile Asp Arg Gly Gly Asp Asn Ala Glu Ser Arg Lys Ala Leu Gly Val
    130                 135                 140

Glu Phe Asp Ile Ile Gly Leu Ser Tyr Tyr Leu Asp Ala Leu Arg Asp
145                 150                 155                 160

Asn Leu His Asp Leu Ala Glu Arg Val Val Glu Thr Ala Tyr Pro Trp
                165                 170                 175
```

```
Thr Leu Glu Gln Pro Asp Asn Gln Glu Leu Leu Pro Gly Tyr
            180                 185                 190

Pro Ala Ser Val Leu Lys Asp Leu Leu Gln Ile Val Arg Glu Val Pro
        195                 200                 205

Gly Gly Tyr Trp Glu Pro Ala Trp Ile Pro Ser Lys Glu Glu Trp Ser
    210                 215                 220

Trp Gly Asn Leu Thr Met Phe Asp Phe Lys Gly Gln Lys Leu Lys Ala
225                 230                 235                 240

Gly Leu Glu Asn Glu Thr Glu Trp Asp Glu Gln Pro
                245                 250

<210> SEQ ID NO 11
<211> LENGTH: 735
<212> TYPE: DNA
<213> ORGANISM: Bacillus agaradhaerens AC13 (DSM 8721)
<220> FEATURE:
<221> NAME/KEY: CDS
<222> LOCATION: (1)..(735)
<223> OTHER INFORMATION: DNA encoding the Galactanase shown in SEQ ID
      NO.12.

<400> SEQUENCE: 11 ttc tac gat aat ggc gta gag aaa gac gct ctg aaa ata ttg aaa gat     48
Phe Tyr Asp Asn Gly Val Glu Lys Asp Ala Leu Lys Ile Leu Lys Asp
  1               5                  10                  15 acc ggt gtt aac tat gaa gac cca gtt aat gtt ggc ggt gcc aat gac     96
Thr Gly Val Asn Tyr Glu Asp Pro Val Asn Val Gly Gly Ala Asn Asp
             20                  25                  30 cta gag gaa aca gtc aaa gaa cac gat atg ggc ttt ctc tta aat ttt    144
Leu Glu Glu Thr Val Lys Glu His Asp Met Gly Phe Leu Leu Asn Phe
         35                  40                  45 cat tac tca aat ttt caa aac aaa ccg act gct tgg gaa gac ttg acg    192
His Tyr Ser Asn Phe Gln Asn Lys Pro Thr Ala Trp Glu Asp Leu Thr
     50                  55                  60 ttt gat gaa tta gtc aca gct gaa acg tta caa gtg cta gaa gaa gtg    240
Phe Asp Glu Leu Val Thr Ala Glu Thr Leu Gln Val Leu Glu Glu Val
 65                  70                  75                  80 gat ggc ctg cca gat gaa att cag tct ggc atg ctg tgg cca gac ggt    288
Asp Gly Leu Pro Asp Glu Ile Gln Ser Gly Met Leu Trp Pro Asp Gly
                 85                  90                  95 aaa aca tgg gga gaa ggt gga ttt gaa aat ctc tta cag tta gta aat    336
Lys Thr Trp Gly Glu Gly Gly Phe Glu Asn Leu Leu Gln Leu Val Asn
            100                 105                 110 gca ggt att gat gcc gag aat cat agt gtg gaa ata atg cta cac ctg    384
Ala Gly Ile Asp Ala Glu Asn His Ser Val Glu Ile Met Leu His Leu
        115                 120                 125 gca gac gga gga gac tgg ttt gat gag atg tta gct cac ggt gtc cat    432
Ala Asp Gly Gly Asp Trp Phe Asp Glu Met Leu Ala His Gly Val His
    130                 135                 140 gac ttt gat gtc att tat tgg cat ggc tcc cta aat gac tta caa gct    480
Asp Phe Asp Val Ile Tyr Trp His Gly Ser Leu Asn Asp Leu Gln Ala
145                 150                 155                 160 aac ttg aat gac atc gac gtg att gtc gtt gaa aca tcc tat gct cac    528
Asn Leu Asn Asp Ile Asp Val Ile Val Val Glu Thr Ser Tyr Ala His
                165                 170                 175 aca ttg gaa gag ggg ttc ggt aca gag gaa gag gtt gaa ggc ggt tat    576
Thr Leu Glu Glu Gly Phe Gly Thr Glu Glu Glu Val Glu Gly Gly Tyr
            180                 185                 190 ccg gcc act gtt gaa gaa gat gtc atg tcg gtc ata cat ggt gtg cca    624
Pro Ala Thr Val Glu Glu Asp Val Met Ser Val Ile His Gly Val Pro
        195                 200                 205
```

```
aat gat cat ggc aga cca aca tgg ata ccg gct gaa aat gct ggt tgg        672
Asn Asp His Gly Arg Pro Thr Trp Ile Pro Ala Glu Asn Ala Gly Trp
    210                 215                 220 aaa gat ggc gaa gga aca ttg ttt gat ttt gac ggt aat gcc tta cca        720
Lys Asp Gly Glu Gly Thr Leu Phe Asp Phe Asp Gly Asn Ala Leu Pro
225                 230                 235                 240 tca tta aag att ttt                                                    735
Ser Leu Lys Ile Phe
                245

<210> SEQ ID NO 12
<211> LENGTH: 245
<212> TYPE: PRT
<213> ORGANISM: Bacillus agaradhaerens AC13 (DSM 8721)

<400> SEQUENCE: 12

Phe Tyr Asp Asn Gly Val Glu Lys Asp Ala Leu Lys Ile Leu Lys Asp
  1               5                  10                  15

Thr Gly Val Asn Tyr Glu Asp Pro Val Asn Val Gly Gly Ala Asn Asp
             20                  25                  30

Leu Glu Glu Thr Val Lys Glu His Asp Met Gly Phe Leu Leu Asn Phe
         35                  40                  45

His Tyr Ser Asn Phe Gln Asn Lys Pro Thr Ala Trp Glu Asp Leu Thr
     50                  55                  60

Phe Asp Glu Leu Val Thr Ala Glu Thr Leu Gln Val Leu Glu Glu Val
 65                  70                  75                  80

Asp Gly Leu Pro Asp Glu Ile Gln Ser Gly Met Leu Trp Pro Asp Gly
                 85                  90                  95

Lys Thr Trp Gly Glu Gly Phe Glu Asn Leu Leu Gln Leu Val Asn
            100                 105                 110

Ala Gly Ile Asp Ala Glu Asn His Ser Val Glu Ile Met Leu His Leu
        115                 120                 125

Ala Asp Gly Gly Asp Trp Phe Asp Glu Met Leu Ala His Gly Val His
    130                 135                 140

Asp Phe Asp Val Ile Tyr Trp His Gly Ser Leu Asn Asp Leu Gln Ala
145                 150                 155                 160

Asn Leu Asn Asp Ile Asp Val Ile Val Glu Thr Ser Tyr Ala His
                165                 170                 175

Thr Leu Glu Glu Gly Phe Gly Thr Glu Glu Val Glu Gly Gly Tyr
            180                 185                 190

Pro Ala Thr Val Glu Glu Asp Val Met Ser Val Ile His Gly Val Pro
        195                 200                 205

Asn Asp His Gly Arg Pro Thr Trp Ile Pro Ala Glu Asn Ala Gly Trp
    210                 215                 220

Lys Asp Gly Glu Gly Thr Leu Phe Asp Phe Asp Gly Asn Ala Leu Pro
225                 230                 235                 240

Ser Leu Lys Ile Phe
                245

<210> SEQ ID NO 13
<211> LENGTH: 891
<212> TYPE: DNA
<213> ORGANISM: Bacillus subtilis
<220> FEATURE:
<221> NAME/KEY: CDS
<222> LOCATION: (1)..(891)
<223> OTHER INFORMATION: DNA encoding the Galactanase shown in SEQ ID
      NO.14.
```

-continued

<400> SEQUENCE: 13

| | | | | | | | | | | | | | | | | |
|---|---|---|---|---|---|---|---|---|---|---|---|---|---|---|---|---|
| atg | ttc | ttt | gcg | gct | gcc | atc | gtg | tgg | agt | gca | tgt | agt | tca | att | gag | 48 |
| Met | Phe | Phe | Ala | Ala | Ala | Ile | Val | Trp | Ser | Ala | Cys | Ser | Ser | Ile | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aag | gag | aag | cac | gtg | tca | gag | ctt | cgg | gca | gag | gat | gag | ggg | atg | aac | 96 |
| Lys | Glu | Lys | His | Val | Ser | Glu | Leu | Arg | Ala | Glu | Asp | Glu | Gly | Met | Asn | |
| | | 20 | | | | | 25 | | | | | 30 | | | | |

| | | | | | | | | | | | | | | | | |
|---|---|---|---|---|---|---|---|---|---|---|---|---|---|---|---|---|
| aag | gat | ttt | atc | aaa | ggg | gca | gat | gta | tcc | aac | agc | ggt | gtc | acc | ttt | 144 |
| Lys | Asp | Phe | Ile | Lys | Gly | Ala | Asp | Val | Ser | Asn | Ser | Gly | Val | Thr | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| tac | aat | aca | aac | gga | aaa | cgc | cag | aaa | cag | gct | ggg | gtc | aac | tat | gtt | 192 |
| Tyr | Asn | Thr | Asn | Gly | Lys | Arg | Gln | Lys | Gln | Ala | Gly | Val | Asn | Tyr | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| cgc | gtc | cgc | atc | tgg | aat | ggc | aac | ggg | tat | ggc | ggg | gga | aac | aat | gat | 240 |
| Arg | Val | Arg | Ile | Trp | Asn | Gly | Asn | Gly | Tyr | Gly | Gly | Gly | Asn | Asn | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtt | caa | aaa | gcc | gcg | aca | gcg | aac | gga | atg | aag | gtg | ctg | gcc | gac | ttt | 288 |
| Val | Gln | Lys | Ala | Ala | Thr | Ala | Asn | Gly | Met | Lys | Val | Leu | Ala | Asp | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| cac | tac | cca | gcg | aaa | caa | aag | gtg | ccc | aaa | gcc | tgg | gcg | aat | ctc | agc | 336 |
| His | Tyr | Pro | Ala | Lys | Gln | Lys | Val | Pro | Lys | Ala | Trp | Ala | Asn | Leu | Ser | |
| | | | | 100 | | | | | 105 | | | | | 110 | | |

| | | | | | | | | | | | | | | | | |
|---|---|---|---|---|---|---|---|---|---|---|---|---|---|---|---|---|
| aag | ctc | tat | gag | tat | acg | aaa | caa | agc | ctg | caa | aag | atg | atc | ggc | atg | 384 |
| Lys | Leu | Tyr | Glu | Tyr | Thr | Lys | Gln | Ser | Leu | Gln | Lys | Met | Ile | Gly | Met | |
| | | | 115 | | | | | 120 | | | | | 125 | | | |

| | | | | | | | | | | | | | | | | |
|---|---|---|---|---|---|---|---|---|---|---|---|---|---|---|---|---|
| gtt | cag | gtc | gga | aat | gaa | aca | aca | gga | gga | ttt | gcc | aag | atg | tgc | caa | 432 |
| Val | Gln | Val | Gly | Asn | Glu | Thr | Thr | Gly | Gly | Phe | Ala | Lys | Met | Cys | Gln | |
| | | 130 | | | | | 135 | | | | | 140 | | | | |

| | | | | | | | | | | | | | | | | |
|---|---|---|---|---|---|---|---|---|---|---|---|---|---|---|---|---|
| tta | ttt | aat | gaa | gga | agc | cga | gcg | gtc | agg | ttg | gtc | gcc | ctg | cat | ttt | 480 |
| Leu | Phe | Asn | Glu | Gly | Ser | Arg | Ala | Val | Arg | Leu | Val | Ala | Leu | His | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| acc | aat | cct | gaa | acg | gct | gga | agg | aca | ctc | agc | aaa | aac | aaa | gtg | gat | 528 |
| Thr | Asn | Pro | Glu | Thr | Ala | Gly | Arg | Thr | Leu | Ser | Lys | Asn | Lys | Val | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| tat | gat | gtg | ttt | gct | agc | cat | ggc | aca | tta | caa | aat | ttg | acc | tcc | gtg | 576 |
| Tyr | Asp | Val | Phe | Ala | Ser | His | Gly | Thr | Leu | Gln | Asn | Leu | Thr | Ser | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | aag | gct | gtt | aaa | gtc | atg | gtg | gcg | gag | aca | tcg | tac | acc | tat | acc | 624 |
| Leu | Lys | Ala | Val | Lys | Val | Met | Val | Ala | Glu | Thr | Ser | Tyr | Thr | Tyr | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| gct | gag | aat | aca | gca | cca | aaa | agc | ggg | cag | acg | ttg | cca | tat | cca | att | 672 |
| Ala | Glu | Asn | Thr | Ala | Pro | Lys | Ser | Gly | Gln | Thr | Leu | Pro | Tyr | Pro | Ile | |
| 210 | | | | | 215 | | | | | 220 | | | | | | |

| | | | | | | | | | | | | | | | | |
|---|---|---|---|---|---|---|---|---|---|---|---|---|---|---|---|---|
| act | gca | gta | aga | gat | gta | atg | gag | gca | gtg | gcg | aat | acg | ggc | ttc | tac | 720 |
| Thr | Ala | Val | Arg | Asp | Val | Met | Glu | Ala | Val | Ala | Asn | Thr | Gly | Phe | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tgg | gag | ccg | gcg | tgg | att | cca | gtc | ggg | ccg | aag | aca | gtg | tta | tgg | gaa | 768 |
| Trp | Glu | Pro | Ala | Trp | Ile | Pro | Val | Gly | Pro | Lys | Thr | Val | Leu | Trp | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| aca | tac | ggg | tca | ggg | tgg | gcg | tcc | agc | tat | gaa | gac | gcc | ggg | aag | tgg | 816 |
| Thr | Tyr | Gly | Ser | Gly | Trp | Ala | Ser | Ser | Tyr | Glu | Asp | Ala | Gly | Lys | Trp | |
| | | | 260 | | | | | 265 | | | | | 270 | | | |

| | | | | | | | | | | | | | | | | |
|---|---|---|---|---|---|---|---|---|---|---|---|---|---|---|---|---|
| tat | ggg | gga | agt | gct | gta | gat | aat | aat | gga | cac | ccg | ctg | cct | tcc | ttg | 864 |
| Tyr | Gly | Gly | Ser | Ala | Val | Asp | Asn | Asn | Gly | His | Pro | Leu | Pro | Ser | Leu | |
| | | 275 | | | | | 280 | | | | | 285 | | | | |

| | | | | | | | | |
|---|---|---|---|---|---|---|---|---|
| cag | gtg | ttt | caa | tat | gcg | aag | aaa | cgc | 891 |
| Gln | Val | Phe | Gln | Tyr | Ala | Lys | Lys | Arg | |
| | | 290 | | | | | 295 | | |

```
<210> SEQ ID NO 14
<211> LENGTH: 297
<212> TYPE: PRT
<213> ORGANISM: Bacillus subtilis

<400> SEQUENCE: 14

Met Phe Phe Ala Ala Ala Ile Val Trp Ser Ala Cys Ser Ser Ile Glu
 1               5                  10                  15

Lys Glu Lys His Val Ser Glu Leu Arg Ala Glu Asp Glu Gly Met Asn
             20                  25                  30

Lys Asp Phe Ile Lys Gly Ala Asp Val Ser Asn Ser Gly Val Thr Phe
         35                  40                  45

Tyr Asn Thr Asn Gly Lys Arg Gln Lys Gln Ala Gly Val Asn Tyr Val
     50                  55                  60

Arg Val Arg Ile Trp Asn Gly Asn Gly Tyr Gly Gly Asn Asn Asp
 65                  70                  75                  80

Val Gln Lys Ala Ala Thr Ala Asn Gly Met Lys Val Leu Ala Asp Phe
                 85                  90                  95

His Tyr Pro Ala Lys Gln Lys Val Pro Lys Ala Trp Ala Asn Leu Ser
            100                 105                 110

Lys Leu Tyr Glu Tyr Thr Lys Gln Ser Leu Gln Lys Met Ile Gly Met
        115                 120                 125

Val Gln Val Gly Asn Glu Thr Thr Gly Gly Phe Ala Lys Met Cys Gln
    130                 135                 140

Leu Phe Asn Glu Gly Ser Arg Ala Val Arg Leu Val Ala Leu His Phe
145                 150                 155                 160

Thr Asn Pro Glu Thr Ala Gly Arg Thr Leu Ser Lys Asn Lys Val Asp
                165                 170                 175

Tyr Asp Val Phe Ala Ser His Gly Thr Leu Gln Asn Leu Thr Ser Val
            180                 185                 190

Leu Lys Ala Val Lys Val Met Val Ala Glu Thr Ser Tyr Thr Tyr Thr
        195                 200                 205

Ala Glu Asn Thr Ala Pro Lys Ser Gly Gln Thr Leu Pro Tyr Pro Ile
    210                 215                 220

Thr Ala Val Arg Asp Val Met Glu Ala Val Ala Asn Thr Gly Phe Tyr
225                 230                 235                 240

Trp Glu Pro Ala Trp Ile Pro Val Gly Pro Lys Thr Val Leu Trp Glu
                245                 250                 255

Thr Tyr Gly Ser Gly Trp Ala Ser Ser Tyr Glu Asp Ala Gly Lys Trp
            260                 265                 270

Tyr Gly Gly Ser Ala Val Asp Asn Asn Gly His Pro Leu Pro Ser Leu
        275                 280                 285

Gln Val Phe Gln Tyr Ala Lys Lys Arg
    290                 295

<210> SEQ ID NO 15
<211> LENGTH: 30
<212> TYPE: DNA
<213> ORGANISM: Bacillus subtilis
<220> FEATURE:
<221> NAME/KEY: misc_feature
<222> LOCATION: (1)..(30)
<223> OTHER INFORMATION: Bacillus galactanase motif.

<400> SEQUENCE: 15
tacacctata ccgctgagga tggcgatggg                                        30
```

```
<210> SEQ ID NO 16
<211> LENGTH: 30
<212> TYPE: DNA
<213> ORGANISM: Bacillus licheniformis
<220> FEATURE:
<221> NAME/KEY: misc_feature
<222> LOCATION: (1)..(30)
<223> OTHER INFORMATION: Bacillus galactanase motif.

<400> SEQUENCE: 16
tatacgtata cggctgaaga cggagacgga                              30

<210> SEQ ID NO 17
<211> LENGTH: 30
<212> TYPE: DNA
<213> ORGANISM: Bacillus agaradhaerens
<220> FEATURE:
<221> NAME/KEY: misc_feature
<222> LOCATION: (1)..(30)
<223> OTHER INFORMATION: Bacillus galactanase motif.

<400> SEQUENCE: 17
tatgctcaca cattggaaga gggggatggt                              30

<210> SEQ ID NO 18
<211> LENGTH: 30
<212> TYPE: DNA
<213> ORGANISM: Bacillus circulans
<220> FEATURE:
<221> NAME/KEY: misc_feature
<222> LOCATION: (1)..(30)
<223> OTHER INFORMATION: Bacillus galactanase motif.

<400> SEQUENCE: 18
tatccttgga cactggagca acctgatggc                              30

<210> SEQ ID NO 19
<211> LENGTH: 30
<212> TYPE: DNA
<213> ORGANISM: Bacillus
<220> FEATURE:
<221> NAME/KEY: misc_feature
<222> LOCATION: (1)..(30)
<223> OTHER INFORMATION: Bacillus galactanase consensus primer.

<400> SEQUENCE: 19
tayncnyrna cnnykgarsa nssngayggn                              30

<210> SEQ ID NO 20
<211> LENGTH: 14
<212> TYPE: PRT
<213> ORGANISM: Bacillus
<220> FEATURE:
<223> OTHER INFORMATION: Bacillus galactanase motif as shown in SEQ ID
      NO.2 but here with more detail
<220> FEATURE:
<223> OTHER INFORMATION: Position 2 in this conserved region is either
      Glutamine (Q) or Leucine (L)
<220> FEATURE:
<223> OTHER INFORMATION: Position 3 is either Threonine (T) or Alanine
      (A)
<220> FEATURE:
<223> OTHER INFORMATION: Position 4 is either Methionine (M) or Leucine
      (L)
<220> FEATURE:
<223> OTHER INFORMATION: Position 13 is either Proline (P) or Glutamine
      (Q)
<220> FEATURE:
<223> OTHER INFORMATION: Xaa at position 2,3,4,8,10,11,13 is any amino
      acid
```

-continued

```
<400> SEQUENCE: 20

Asn Xaa Xaa Xaa Phe Asp Phe Xaa Gly Xaa Xaa Leu Xaa Ser
  1               5                  10

<210> SEQ ID NO 21
<211> LENGTH: 42
<212> TYPE: DNA
<213> ORGANISM: Bacillus subtilis
<220> FEATURE:
<221> NAME/KEY: misc_feature
<222> LOCATION: (1)..(42)
<223> OTHER INFORMATION: Bacillus galactanase motif.

<400> SEQUENCE: 21
aatcaagctt tatttgattt taatggacac ccgctgcctt cc                    42

<210> SEQ ID NO 22
<211> LENGTH: 42
<212> TYPE: DNA
<213> ORGANISM: Bacillus licheniformis
<220> FEATURE:
<221> NAME/KEY: misc_feature
<222> LOCATION: (1)..(42)
<223> OTHER INFORMATION: Bacillus galactanase motif.

<400> SEQUENCE: 22
aatcaggcat tgtttgattt taaaggacgt ccattgccgt cg                    42

<210> SEQ ID NO 23
<211> LENGTH: 42
<212> TYPE: DNA
<213> ORGANISM: Bacillus agaradhaerens
<220> FEATURE:
<221> NAME/KEY: misc_feature
<222> LOCATION: (1)..(42)
<223> OTHER INFORMATION: Bacillus galactanase motif.

<400> SEQUENCE: 23
aaccaaacat tgtttgattt tgacggtaat gccttaccat ca                    42

<210> SEQ ID NO 24
<211> LENGTH: 42
<212> TYPE: DNA
<213> ORGANISM: Bacillus circulans
<220> FEATURE:
<221> NAME/KEY: misc_feature
<222> LOCATION: (1)..(42)
<223> OTHER INFORMATION: Bacillus galactanase motif.

<400> SEQUENCE: 24
aacctgacga tgtttgactt caagggccag aagttgcaat cg                    42

<210> SEQ ID NO 25
<211> LENGTH: 42
<212> TYPE: DNA
<213> ORGANISM: Bacillus
<220> FEATURE:
<221> NAME/KEY: misc_feature
<222> LOCATION: (1)..(42)
<223> OTHER INFORMATION: Bacillus galactanase consensus primer.

<400> SEQUENCE: 25
aaycwrrcnw trtttgaytt yranggnmrn nmnytrcmnt cn                    42

<210> SEQ ID NO 26
<211> LENGTH: 24
```

```
<212> TYPE: DNA
<213> ORGANISM: Bacillus subtilis
<220> FEATURE:
<221> NAME/KEY: misc_feature
<222> LOCATION: (1)..(24)
<223> OTHER INFORMATION: Bacillus galactanase motif.

<400> SEQUENCE: 26
tcctattatc ctttctggca tggc                                           24

<210> SEQ ID NO 27
<211> LENGTH: 24
<212> TYPE: DNA
<213> ORGANISM: Bacillus licheniformis
<220> FEATURE:
<221> NAME/KEY: misc_feature
<222> LOCATION: (1)..(24)
<223> OTHER INFORMATION: Bacillus galactanase motif.

<400> SEQUENCE: 27
tcgtattatc cgttttggca tggc                                           24

<210> SEQ ID NO 28
<211> LENGTH: 24
<212> TYPE: DNA
<213> ORGANISM: Bacillus agaradhaerens
<220> FEATURE:
<221> NAME/KEY: misc_feature
<222> LOCATION: (1)..(24)
<223> OTHER INFORMATION: Bacillus galactanase motif.

<400> SEQUENCE: 28
tcgtattatc cttattggca tggc                                           24

<210> SEQ ID NO 29
<211> LENGTH: 24
<212> TYPE: DNA
<213> ORGANISM: Bacillus circulans
<220> FEATURE:
<221> NAME/KEY: misc_feature
<222> LOCATION: (1)..(24)
<223> OTHER INFORMATION: Bacillus galactanase motif.

<400> SEQUENCE: 29
tcttattatc cctggtggca tgga                                           24

<210> SEQ ID NO 30
<211> LENGTH: 24
<212> TYPE: DNA
<213> ORGANISM: Bacillus
<220> FEATURE:
<221> NAME/KEY: misc_feature
<222> LOCATION: (1)..(24)
<223> OTHER INFORMATION: Bacillus galactanase consensus primer.

<400> SEQUENCE: 30
tcntattatc cntnntggca tggm                                           24

<210> SEQ ID NO 31
<211> LENGTH: 27
<212> TYPE: DNA
<213> ORGANISM: Bacillus subtilis
<220> FEATURE:
<221> NAME/KEY: misc_feature
<222> LOCATION: (1)..(27)
<223> OTHER INFORMATION: Bacillus galactanase motif.

<400> SEQUENCE: 31
```
tatgattcaa atggcaacgg gtatggc            27

<210> SEQ ID NO 32
<211> LENGTH: 27
<212> TYPE: DNA
<213> ORGANISM: Bacillus licheniformis
<220> FEATURE:
<221> NAME/KEY: misc_feature
<222> LOCATION: (1)..(27)
<223> OTHER INFORMATION: Bacillus galactanase motif.

<400> SEQUENCE: 32
tatgatgcca acggcaacgg ctacgga            27

<210> SEQ ID NO 33
<211> LENGTH: 27
<212> TYPE: DNA
<213> ORGANISM: Bacillus
<220> FEATURE:
<221> NAME/KEY: misc_feature
<222> LOCATION: (1)..(27)
<223> OTHER INFORMATION: Bacillus galactanase consensus primer.

<400> SEQUENCE: 33
tatgatkcma ayggcaacgg stayggm            27

<210> SEQ ID NO 34
<211> LENGTH: 129
<212> TYPE: DNA
<213> ORGANISM: Bacillus subtilis
<220> FEATURE:
<221> NAME/KEY: misc_feature
<222> LOCATION: (1)..(129)
<223> OTHER INFORMATION: Bacillus galactanase motif.

<400> SEQUENCE: 34
gtcgggccga agacacagat agagaaaaac aaagtgttat gggaaacata cgggtcaggg    60
tgggcgtcca gctatgctgc tgaatacgac cctgaagacg ccgggaagtg gtatggggga   120
agtgctgta                                                          129

<210> SEQ ID NO 35
<211> LENGTH: 129
<212> TYPE: DNA
<213> ORGANISM: Bacillus licheniformis
<220> FEATURE:
<221> NAME/KEY: misc_feature
<222> LOCATION: (1)..(129)
<223> OTHER INFORMATION: Bacillus galactanase motif.

<400> SEQUENCE: 35
gtaggaccgg ctcaccggct cgagaaaaat aaagcgcttt gggagacata cggatcaggc    60
tgggctacaa gctatgctgc tgaatatgac ccggaagacg caggaaagtg gtttggcggc   120
agcgccgta                                                          129

<210> SEQ ID NO 36
<211> LENGTH: 129
<212> TYPE: DNA
<213> ORGANISM: Bacillus
<220> FEATURE:
<221> NAME/KEY: misc_feature
<222> LOCATION: (1)..(129)
<223> OTHER INFORMATION: Bacillus galactanase consensus primer.

<400> SEQUENCE: 36
gtmggrccgr mkmmmcrgmt mgagaaaaay aaagygytwt ggaracata cggrtcaggc    60

```
tgggckwcma gctatgctgc tgaataygac cckgaagacg cmggraagtg gtwtggsggm    120 agygcygta                                                            129
```

<210> SEQ ID NO 37
<211> LENGTH: 24
<212> TYPE: DNA
<213> ORGANISM: Bacillus subtilis
<220> FEATURE:
<221> NAME/KEY: misc_feature
<222> LOCATION: (1)..(24)
<223> OTHER INFORMATION: Bacillus galactanase motif.

<400> SEQUENCE: 37

```
ggaggatttg ccggtgagac tgat                                           24
```

<210> SEQ ID NO 38
<211> LENGTH: 24
<212> TYPE: DNA
<213> ORGANISM: Bacillus licheniformis
<220> FEATURE:
<221> NAME/KEY: misc_feature
<222> LOCATION: (1)..(24)
<223> OTHER INFORMATION: Bacillus galactanase motif.

<400> SEQUENCE: 38

```
gggggccttg ccggtgaaac ggat                                           24
```

<210> SEQ ID NO 39
<211> LENGTH: 24
<212> TYPE: DNA
<213> ORGANISM: Bacillus
<220> FEATURE:
<221> NAME/KEY: misc_feature
<222> LOCATION: (1)..(24)
<223> OTHER INFORMATION: Bacillus galactanase consensus primer.

<400> SEQUENCE: 39

```
ggrggmyttg ccggtgarac kgat                                           24
```

<210> SEQ ID NO 40
<211> LENGTH: 187
<212> TYPE: DNA
<213> ORGANISM: Bacillus licheniformis
<220> FEATURE:
<223> OTHER INFORMATION: Partial galactanase.

<400> SEQUENCE: 40

```
cgaaacaaac gggggccttg ccggtgaaac ggattgggcg aagatgagcc aattattcaa    60
cgccgggagt caagcggtgc gagagacgga ttcgaatatc ctagtcgcct tgcattttac   120
caatccggag acgtcaggaa ggtacgcttg gattgccgag acgcttcatc ggcatcatgt   180
agactac                                                             187
```

<210> SEQ ID NO 41
<211> LENGTH: 61
<212> TYPE: DNA
<213> ORGANISM: Bacillus licheniformis
<220> FEATURE:
<223> OTHER INFORMATION: Partial galactanase.

<400> SEQUENCE: 41

```
ggagacgtca ggaaggtacg cttggattgc cgagacgctt catcggcatc atgtagacta    60
c                                                                    61
```

<210> SEQ ID NO 42
<211> LENGTH: 214
<212> TYPE: DNA
<213> ORGANISM: Bacillus licheniformis
<220> FEATURE:
<223> OTHER INFORMATION: Partial galactanase.

<400> SEQUENCE: 42
tgagacatct tatacgtata cggctgaaga cggagacgga cacggaaata cagctccgaa     60
aaacggccaa acgctgaata atccggtcac cgttcaaggg caggcgaacg cggtccgtga    120
tgtgattcaa gcggtcagcg acgtaggtga agccggaatc ggcgttttct attgggaacc    180
ggcatggatt ccggtaggac cggctcaccg gctc                                214

<210> SEQ ID NO 43
<211> LENGTH: 107
<212> TYPE: DNA
<213> ORGANISM: Bacillus licheniformis
<220> FEATURE:
<223> OTHER INFORMATION: Partial galactanase.

<400> SEQUENCE: 43
acgcggtccg tgatgtgatt caagcggtca gcgacgtagg tgaagccgga atcggcgttt     60
tctattggga accggcatgg attccggtag gaccggctca ccggctc                  107

<210> SEQ ID NO 44
<211> LENGTH: 35
<212> TYPE: DNA
<213> ORGANISM: Bacillus licheniformis
<220> FEATURE:
<223> OTHER INFORMATION: Partial galactanase.

<400> SEQUENCE: 44
ccgtgatgtg attcaagcgg tcagcgacgt aggtg                                35

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(42)
<223> OTHER INFORMATION: Primer: #LWN5494

<400> SEQUENCE: 45
gtcgccgggg cggccgctat caattggtaa ctgtatctca gc                        42

<210> SEQ ID NO 46
<211> LENGTH: 64
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(64)
<223> OTHER INFORMATION: Primer #LWN5495

<400> SEQUENCE: 46
gtcgcccggg agctctgatc aggtaccaag cttgtcgacc tgcagaatga ggcagcaaga     60
agat                                                                 64

```
<210> SEQ ID NO 47
<211> LENGTH: 61
<212> TYPE: DNA
<213> ORGANISM: Artificial Sequence
<220> FEATURE:
<221> NAME/KEY: misc_feature
<222> LOCATION: (1)..(61)
<223> OTHER INFORMATION: Primer: #LWN5938
<220> FEATURE:
<223> OTHER INFORMATION: Description of Artificial Sequence: Primer

<400> SEQUENCE: 47
gtcggcggcc gctgatcacg taccaagctt gtcgacctgc agaatgaggc agcaagaaga      60
t                                                                     61

<210> SEQ ID NO 48
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Primer: #LWN5939
<220> FEATURE:
<223> OTHER INFORMATION: Description of Artificial Sequence: Primer

<400> SEQUENCE: 48
gtcggagctc tatcaattgg taactgtatc tcagc                                 35

<210> SEQ ID NO 49
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Primer: #LWN7864
<220> FEATURE:
<223> OTHER INFORMATION: Description of Artificial Sequence: Primer

<400> SEQUENCE: 49
aacagctgat cacgactgat cttttagctt ggcac                                 35

<210> SEQ ID NO 50
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Primer: #LWN7901
<220> FEATURE:
<223> OTHER INFORMATION: Description of Artificial Sequence: Primer

<400> SEQUENCE: 50
aactgcagcc gcggcacatc ataatgggac aaatggg                               37

<210> SEQ ID NO 51
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Primer: Galactanase.B.lich.upper.SacII
<220> FEATURE:
<223> OTHER INFORMATION: Description of Artificial Sequence: Primer

<400> SEQUENCE: 51
```

```
tctgcagccg cggcacacag agattcaggg acggc                              35

<210> SEQ ID NO 52
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Galactanase.B.lich.lower.NotI
<220> FEATURE:
<223> OTHER INFORMATION: Description of Artificial Sequence: Primer

<400> SEQUENCE: 52
gcgttgagaa gcggccgccg gcctttttc cattctgc                            38
```